(12) United States Patent
Maher

(10) Patent No.: US 8,702,631 B2
(45) Date of Patent: Apr. 22, 2014

(54) VESTIBULAR STIMULATION SYSTEMS AND METHODS

(75) Inventor: Kevin Maher, Colorado Springs, CO (US)

(73) Assignee: Ultrathera Technologies Inc., Colorado Springs, CO (US)

(*) Notice: Subject to any disclaimer, the term of this patent is extended or adjusted under 35 U.S.C. 154(b) by 299 days.

(21) Appl. No.: 12/744,896

(22) PCT Filed: Nov. 26, 2008

(86) PCT No.: PCT/IB2008/003667
§ 371 (c)(1),
(2), (4) Date: Oct. 22, 2010

(87) PCT Pub. No.: WO2009/068994
PCT Pub. Date: Jun. 4, 2009

(65) Prior Publication Data
US 2011/0028872 A1    Feb. 3, 2011

Related U.S. Application Data

(60) Provisional application No. 60/990,060, filed on Nov. 26, 2007.

(51) Int. Cl.
*A61H 1/00* (2006.01)
(52) U.S. Cl.
USPC .................. 601/26; 601/24; 601/84; 601/86

(58) Field of Classification Search
USPC .......... 601/24–26, 85, 86; 434/30, 34–35, 51, 434/55, 59; 600/552, 558, 595; 104/53; 472/29, 30, 32, 33, 35, 40–42, 44, 45
See application file for complete search history.

(56) References Cited

U.S. PATENT DOCUMENTS

| | | | |
|---|---|---|---|
| 4,634,146 A * | 1/1987 | Yaniv | 281/15.1 |
| 4,710,128 A * | 12/1987 | Wachsmuth et al. | 434/46 |
| 5,285,685 A | 2/1994 | Chelette | |
| 5,759,107 A * | 6/1998 | Nagel | 472/47 |
| 5,919,149 A | 7/1999 | Allum | |
| 5,983,128 A | 11/1999 | Baudonniere et al. | |
| 6,063,046 A | 5/2000 | Allum | |
| 6,383,150 B1 | 5/2002 | Stewart et al. | |
| 6,656,137 B1 | 12/2003 | Tyldsley et al. | |
| 6,796,947 B2 | 9/2004 | Watt et al. | |
| 6,800,062 B2 * | 10/2004 | Epley | 600/558 |

(Continued)

FOREIGN PATENT DOCUMENTS

RU    2114772    7/1998

OTHER PUBLICATIONS

Benson, AJ, "Motion Sickness", in Vertigo / edited by MR Dix et al, New York: Wiley (1984), pp. 391-426.*

(Continued)

*Primary Examiner* — Justine Yu
*Assistant Examiner* — Douglas Sul
(74) *Attorney, Agent, or Firm* — Polsinelli PC

(57) ABSTRACT

A method of and system for administering a dose of vestibular stimulation to a subject comprising a rotational device comprising at least a first axis of rotation and configured to allow continuous rotation through more than 360 degrees around each axis of rotation are provided.

11 Claims, 16 Drawing Sheets

(56) References Cited

U.S. PATENT DOCUMENTS

| | | | |
|---|---|---|---|
| 7,285,099 B1 * | 10/2007 | Peterka | 600/559 |
| 7,559,766 B2 * | 7/2009 | Epley et al. | 434/34 |
| 8,066,651 B2 * | 11/2011 | Richard Vitton | 601/24 |
| 2004/0097839 A1 * | 5/2004 | Epley | 600/595 |
| 2007/0167886 A1 | 7/2007 | Epley | |

OTHER PUBLICATIONS

Chee et al., "Semicircular Canal Stimulation in Cerebral Palsied Children", Physical Therapy, Sep. 1978, pp. 1071-1075, vol. 58, No. 9.

Reason, "Motion Sickness Adaptation: A Neural Mismatch Model", Journal of the Royal Society of Medicine, Nov. 1978, pp. 819-823, vol. 71, <URL: http://www.pubmedcentral.nih.gov/picrender.fcgi?artid=1436193&blobtype=pdf>.

Magrun, et al., "Effects of Vestibular Stimulation on Spontaneous Use of Verbal Language in Developmentally Delayed Children", The American Journal of Occupational Therapy, Feb. 1981, pp. 101-104, vol. 35, No. 2.

MacLean Jr., et al., "Effects of Vestibular Stimulation on Motor Development and Stereotyped Behavior of Developmentally Delayed Children", Journal of Abnormal Child Psychology, Sep. 1981, pp. 229-245, vol. 10, No. 2.

Ottenbacher, "Developmental Implications of Clinically Applied Vestibular Stimulation", Physical Therapy, Mar. 1983, pp. 338-342, vol. 63, No. 3.

Slavik et al., "Vestibular Stimulation and Eye Contact in Autistic Children", Neuropediatrics, Feb. 1984, pp. 33-36, vol. 15.

Benson, "Motion Sickness", Vertigo, edited by MR Dix et al., New York: Wiley, 1984, pp. 391-426.

Ray et al., "The Effectiveness of Self-Initiated Vestibular Stimulation in Producing Speech Sounds in an Autistic Child", Occupational Therapy Journal of Research, May/Jun. 1988, pp. 186-190, vol. 8, No. 3.

Uyanik, et al., "Comparison of Different Therapy Approaches in Children with Down Syndrome", Pediatrics International, 2003, pp. 68-73, vol. 45.

Andersen, R. A., "Multimodal integration for the representation of space in the posterior parietal cortex," *Phil. Trans. R. Soc. Lond.*, (1997), 352: 1421-1428.

Bhidayasiri, R. et al., "Pathophysiology of slow vertical saccades in progressive supranuclear palsy," *Neurology*, (2001), 57: 2070-2077.

Cai, R. H. et al., "Vestibular signals can distort the perceived spatial relationship of retinal stimuli," *Exp Brain Res*, (2000), 135: 275-278.

Israel, I. et al., "Vestibular information contributes to update retinotopic maps," *NeuroReport*, (1999), 10: 3479-3483.

Kanayama, R. et al., "Perceptual studies in patients with vestibular neurectomy," *Acta Otolaryngol*, (1995), Suppl 520: 408-411.

Koenig, E. et al., "A new multiaxis rotating chair for oculomotor and vestibular function testing in humans," *Neuro-opthalmology*, (1996) 16(3): 157-162.

Seidman, S. H. et al., "The human torsional vestibulo-ocular reflex during rotation about an earth-vertical axis," *Brain Research*, (1989) 504: 264-268.

Seidman S. H. et al, "Dynamic properties of the human vestibulo-ocular reflex during head rotations in roll," *Vision Research*, (1995), 35 (5): 679-689.

\* cited by examiner

VESTIBULAR STIMULATION SYSTEMS AND METHODS

This application is the national phase entry under 35 U.S.C.§371 of International Patent Application No. PCT/IB2008/003667, which claims benefit under 35 U.S.C. §119 (e) of U.S. Provisional Application Ser. No. 60/990,060, both of which are incorporated by reference in their entirety.

FIELD

The present disclosure relates to vestibular stimulation systems, control systems, doses of stimulation, and methods of use.

BACKGROUND

The primary functions of the vestibular system are maintaining balance (posture and equilibrium) by monitoring motion of the head, and stabilizing the eyes relative to the environment. There are two components to monitoring motion: detecting angular acceleration (i.e. detecting changes in rotation) and detecting linear acceleration (i.e. detecting changes along a line, such as gravitational changes or changes in forward motion). Secondary functions of the vestibular system are to provide critical information for sensory system integration. Sensory integration is the ability of the central nervous system to gather current information such as movement, touch, taste, smell, vision, and hearing to put them together with prior information, memories, and knowledge stored in the brain to make a meaningful and appropriate response to one's environment.

Disorders of the vestibular system in individuals has been linked to a number of developmental disorders. Studies have shown that stimulating the vestibular system of subjects has resulted in improved motor control, social behavior, and balance. Chee et al. (Phys Ther. 1978 September; 58(9):1071-5) observed improved reflex and gross motor skills. Vestibular stimulation has also been used to treat developmentally delayed subjects. MacLean and Baumeister (J Abnorm Child Psychol. 1982 June; 10(2):229-45) provided vestibular stimulation to developmentally delayed babies by rotating the children in a motor-driven chair at a constant velocity. The acceleration was not measured. Ottenbacher (1: Phys Ther. 1983 March; 63(3):338-42) used vestibular stimulation to improve neuromotor development in high-risk infants and developmentally delayed children. Magrun et al. (Am J Occup Ther. 1981 February; 35(2):101-4) showed an increase in spontaneous verbal language use for primary trainable mentally deficient and developmentally retarded preschoolers immediately after the stimulation periods. Uyanik et al. (Pediatrics International Volume 45 Issue 1 Page 68-February 2003) tested vestibular stimulation on children with Down syndrome. Sensory integration, vestibular stimulation and neurodevelopmental therapy were effective in children with Down syndrome. Ray et al. (THE OCCUPATIONAL THERAPY JOURNAL OF RESEARCH 83, pg. 187-191) showed the effect of vestibular stimulation resulted in an increased percentage of vocalizations when an autistic child used a swing for vestibular stimulation. Slavik et al. (Neuropediatrics. 1984 February; 15(1):33-6) showed increased duration of eye contact for autistic boys on hand-operated oscillating swing.

Most protocols for applying vestibular stimulation only applied an angular acceleration at the very beginning and end of the profile, for a total of approximately four seconds. For example, when a subject is accelerated to a constant velocity, the only acceleration felt by the subject occurs during acceleration and deceleration. Subjects thus were accelerated to a constant velocity. After acceleration to a constant velocity, the stimulus to the semi-circular canals dampens; in fact, in the absence of visual input, the subject will no longer feel they are spinning. Further, previous methods of applying vestibular stimulation are not measurable, repeatable, or conducive to applying different patterns in different directions.

There is therefore a need for systems designed to apply accelerations and decelerations in reproducible and repeatable fashion. This and other needs are addressed by the present invention.

SUMMARY

Vestibular stimulation systems, control systems, doses, and methods of use are provided. Generally, the vestibular stimulation system disclosed includes a restraint system (e.g. a chair) that holds a subject in a position relative to the system. The subject can then be rotated around one, two, or three rotational axes individually or simultaneously in a controlled manner. A computer system controls the vestibular system function and collects and stores data. Specific amounts or doses of stimuli can be administered. Physiological responses to various types of vestibular stimulation can then be tested and recorded.

Methods of administering vestibular stimulation to a subject are also provided. Quantifiable and repeatable measures of vestibular stimulation can be administered in each axis, which can be placed under separate control. Controlled rotation around one, two or three separately controlled vectors in a controlled manner using measured amounts of vestibular stimulation may be accomplished. The intensity of acceleration, frequency of acceleration, and duration of administration can all be varied independently for each axis. The methods include therapeutic and balance training uses, as well as diagnostic uses.

BRIEF DESCRIPTION OF THE DRAWINGS

The following figures are exemplary, and merely describe aspects of the invention.

DETAILED DESCRIPTION

A vestibular stimulation administration system and methodology is provided which employs a computer controlled multi-axis rotational motion device to move a human subject in specific controllable motions with specific controllable angular acceleration (as used herein, acceleration refers to a change in velocity, including acceleration or deceleration relative to an axis of rotation). The system provides for continuous 360 degree rotations through space, capable of inducing a quantifiable amount of passive and active cross-coupled vestibular stimulation and other sensory system stimulation including but not limited to tactile, proprioceptive, somatosensory, auditory and visual stimulation. In one configuration, the vestibular stimulation device is programmably controlled to individually and/or collectively accelerate, decelerate, or maintain angular velocity of two or three axes of rotation allowing for vestibular stimulation in controllable ways. The device allows for multiple and continuous angular accelerations and maintaining angular velocities in the absence of acceleration.

The operating software and computer controlled systems manage all aspects of the rotating device and the safety monitoring components. The computer and software collects human physiological and neurological streaming data from an array of sensors, and displays it concurrent to the real time graphical representation of the applied stimuli which provides a new method for tracking the instantaneous physiological and neurological response to this type of applied stimuli. The data is archived and can be used to quantify progress over time.

The system, apparatus and method conforming to aspects of the present invention offer new opportunities for many different subject populations including subjects with incapacitating disabilities where typical vestibular stimulation exercises might not be manageable or tolerable to subjects with damage to the vestibular system, sensory system integration dysfunction or trauma, cerebral palsy, geriatrics, or other physically and neurologically disabled populations, to receive safe, controllable, quantifiable, and repeatable amounts of vestibular stimulation, not heretofore available.

I. Vestibular Stimulation

In various embodiments, the systems described herein are used to administer vestibular stimulation to a subject.

Figure 6A:
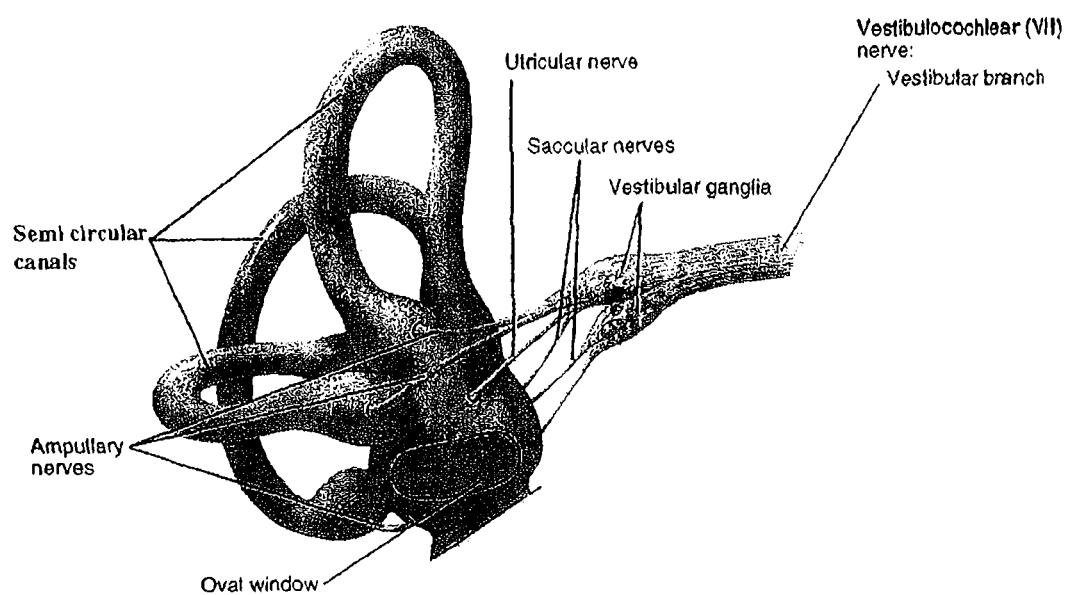
FIG. 6A depicts the vestibular system and associated nerve endings carrying signals to the brain.
Figure 6B:
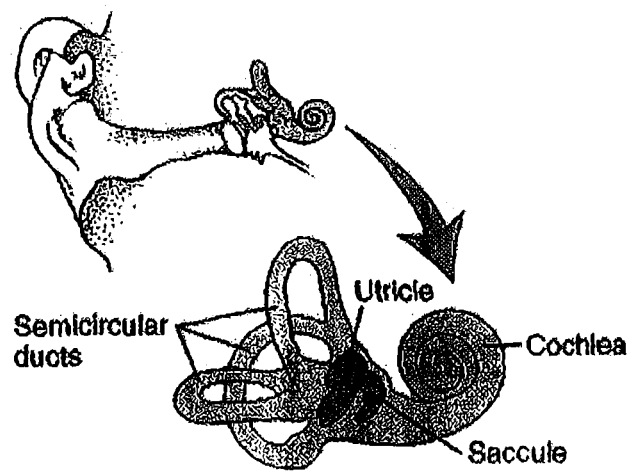
FIG. 6B depicts the vestibular system organs and their orientation in the inner ear.

The vestibular system is depicted in FIGS. 6A and 6B. The vestibular system is located in the inner ear and includes three semi-circular canals and five sense organs: the utricle, the saccule and three ampullae (one for each semi-circular canal). The sense organs house the sensory hair receptors, the maculae (for the utricle and saccule) and cristae (ampullae). These organs are innervated by bipolar cells of the vestibular ganglion that project to the vestibular nucleus in the brainstem. Some vestibular afferents bypass the vestibular nucleus and terminate directly in the flocculonodular lobe of the cerebellum. The utricle and saccule are attached structures in the inner ear which register changes in gravity as an individual moves toward or away from the ground.

Rotational Vestibular Stimulation

The semi-circular canals detect angular acceleration of a subject's head. There are 3 canals, corresponding to the three dimensions of movement. Each canal detects motion in a single plane. Angular accelerations (either clockwise or counterclockwise) are detected by changes in cupula, a gelatinous mass in each canal. The canals are arranged in three distinct planes. Changes in rotational movement in one of three directions result in a change in cupula detected by hairs in the ampula of each canal. Increases in angular acceleration thus result in detecting of a change in rotational motion in at least one of three angular directions. When the subject returns to constant velocity, the cupula returns to equilibrium. Decelerations are detected in the opposite direction. Further, differences in angular acceleration detected in similarly oriented canals in each ear can result in altered vertigo or nausea.

The vestibular system generates compensatory movements with the extraocular eye muscles to compensate for motion via the vestibulo-ocular reflex (VOR), otherwise known as the oculomotor reflex. Vestibular control is thus important for correctly developed vision and responsiveness.

Angular vestibular stimulation refers to changes in angular acceleration provided by the vestibular stimulation device. In various embodiments, angular vestibular stimulation can be administered by administering measured changes in angular acceleration in one or more directions. In various embodiments, the dose can be administered in pitch, yaw, roll, or a combination thereof.

Linear Vestibular Stimulation

Linear vestibular stimulation, such as linear changes in acceleration and the pull of gravity, is mediated by the utricle and saccule depicted in FIG. 6B. Each organ has a sheet of hair cells (the macula) whose cilia are embedded in a gelatinous mass. Unlike the canals, however, this gel has a clump of small crystals embedded in it, called an otolith. The otolith gel mass provides inertia dragging on the hair cells.

Hair cells in the utricle and saccule are polarized and arrayed different directions so that a single sheet of hair cells can detect motion forward and back as well as side to side, thereby covering two dimensions of movement. The utricle lies horizontally in the ear, and detects motion in the horizontal plane. The saccule is oriented vertically, so detects motion in the sagittal plane (up and down, forward and back).

A major role of the saccule and utricle is to maintain vertical orientation with respect to gravity. The linear vestibular system thus compensates for balance. The vestibular nucleus contains four subnuclei: superior, inferior lateral and medial nuclei. Input from the maculae goes to the lateral, inferior and medial nuclei. These nuclei project to spinal motor nuclei via the lateral and medial vestibulospinal tracts that are involved in postural balance. The lateral VST facilitates the action of the antigravity (extensor) muscles while the medial VST mainly influences the activity of the axial muscles of the head and neck (i.e. the head righting reflex). The superior and lateral vestibular nuclei also interact with the flocculonodular lobe of cerebellum.

The systems described herein provide doses of vestibular stimulation by linear vestibular stimulation.

II. Mechanical Rotation System

In various aspects of the present invention, apparatuses configured to rotate around two dimensional (pitch and yaw) and three dimensional (pitch yaw and roll) are provided. The device is rotatably coupled to a frame. The vestibular stimulation devices described herein are configured to allow rotation independently in two or three axes of rotation. The device is further configured to rotate continuously through 360 degrees of freedom in each axis of rotation at independently controlled accelerations. The devices described herein are thus able to vary vestibular stimulation (i.e. acceleration) in continuous fashion.

A. Two Dimensional Rotation and Acceleration

Figure 1:
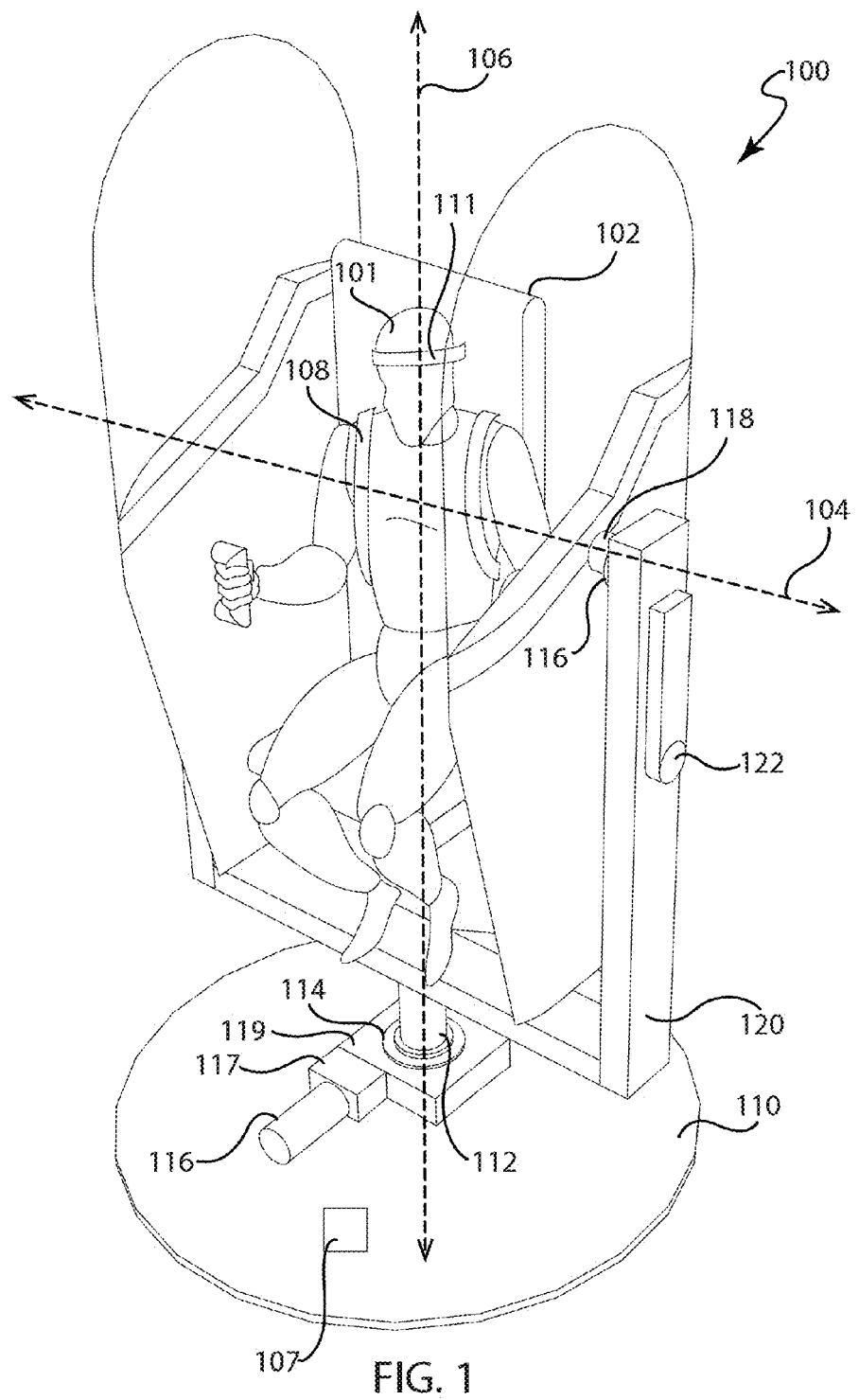
FIG. 1 depicts a vestibular stimulation system configured to rotate around two axes of rotation.

A first embodiment of the mechanical portion of a vestibular stimulation system described herein is depicted in FIG. 1. Vestibular stimulation system 100 includes pitch axis 104 and yaw axis 106. Subject 101 thus can be rotated around both pitch axis 104 and/or yaw axis 106.

Rotation of subject 101 around yaw axis 106 is mediated by yaw shaft 112. Chair 102 is rotationally supported on a base 110 via yaw shaft 112. Yaw shaft 112 is operably linked to support frame 120. A U-shaped support frame 120 rotationally supports chair 102. Yaw shaft 112 is rotationally associated with base 110 via rotational bearing system 114. Chair 102 can thus rotate freely and continuously around yaw axis 106 relative to base 110.

Chair 102 is rotated around yaw axis 106 by yaw axis motor 116. Motor 116 receives power and signals from motor drive computer 107 Yaw axis motor 116 is operably linked to gear reducer 117, which is operably linked to gearbox 119. Yaw axis motor causes rotation of rotational shaft 112 via gear reducer 117 and gearbox 119. When in operation, yaw axis motor 116 provides for rotation around yaw axis 106 in either clockwise or counter-clockwise yaw rotational directions. Further, yaw axis motor 116 can cause rotational acceleration or deceleration in either clockwise or counter-clockwise yaw directions. Rotation around yaw axis 106 can be continuous indefinitely in a single rotational direction, without any limitation on the rotation characteristics or number of rotations. As discussed in more detail below, the computer system is in communication with the yaw axis motor to control acceleration, deceleration, and velocity.

Likewise, chair 102 is operably linked to pitch shaft 118 on a first side and a second pitch shaft on the opposing side (not shown). Pitch shaft 118 is operably associated with bearing cases 114 and 116 at opposing ends of pitch shaft 118. Bearing cases 114 and 116 are operably associated with support frame 120. Rotation of chair 102 around pitch axis 104 is provided by rotating chair 102 around pitch axis 104.

Chair 102 is rotated around pitch axis 104 by pitch axis motor 122. Pitch axis motor 122 is operably associated with pitch rotational shaft 118. Pitch axis motor 122 can rotate chair 102 around pitch axis 104 in either forward or backward pitch rotational directions. Further, pitch axis motor 122 can cause rotational acceleration or deceleration in either clockwise or counter-clockwise pitch directions. There are no intermediate hindrances to rotation when chair 102 rotates around pitch axis 104. Rotation around pitch axis 104 thus can be continuous in a single rotational direction indefinitely, without any limitation on the number of rotations.

A subject who is treated with vestibular stimulation is attached to chair 102 by attachment system 108 to stabilize the subject in the chair during operation. Attachment system 108 components can include shoulder harness 110, head harness 111, and/or lap belt (not shown). Without being held to a specific embodiment, those of skill in the art will recognize that attachment system 108 can vary to include any attachment system known in the art. The spatial orientation of the subject relative to chair 102 is thus maintained.

In operation, rotation of chair 102 around pitch axis 104 and yaw axis 106 are independent, and can occur either separately or simultaneously. Rotation and/or acceleration around pitch axis 104 and/or yaw axis 106 thus can produce a nearly infinite range of motion profiles.

Each axis of the current mechanical device can rotate freely, without mechanical impediment such as wiring or mechanical hindrances. The configuration allows a dose of vestibular stimulation to be administered as a clockwise acceleration in one direction. Once a new velocity is reached, the device no longer accelerates (i.e. the acceleration is zero), and the constant velocity (with zero acceleration) can be maintained indefinitely. A second angular acceleration can be administered around the same axis as the first dose by administering a second acceleration in the same direction as the first acceleration.

Though the embodiment of FIG. 1 depicts pitch axis 104 and yaw axis 106 intersecting at a single point, those of skill in the art will recognize that in various embodiments the axes of rotation are not required to intersect. The axes can be offset relative to each other, or relative to the center of mass of the system.

B. Three Dimensional Vestibular Stimulation System

In this implementation, a chair is rotationally supported in three separate axes. Each axis is coupled to a separate motor that are controlled or programmed independently by a computer controller. The device thus allows continuous rotation and control in each axis of rotation independently.

Figure 2:
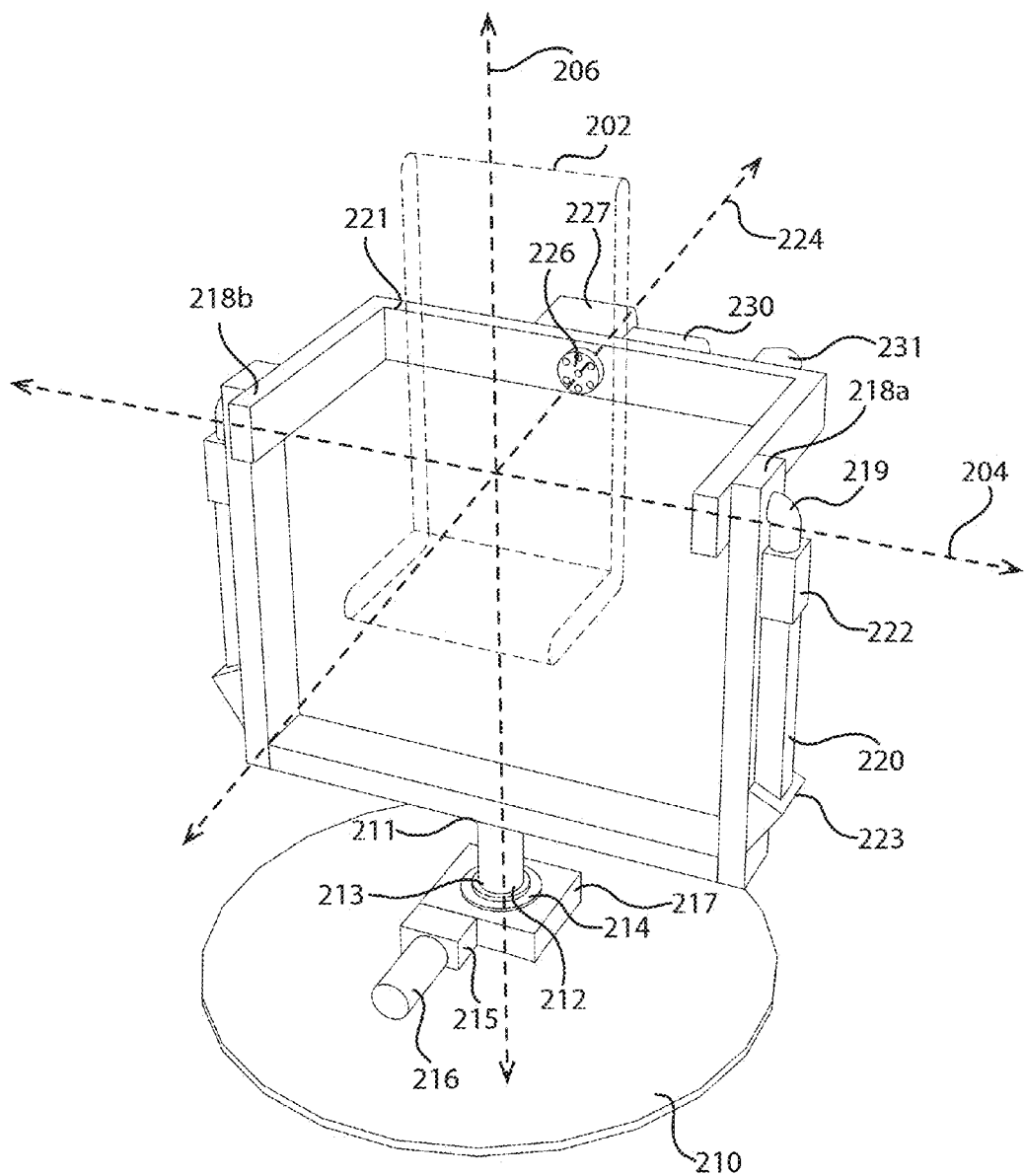
FIG. 2 depicts a vestibular stimulation system configured to rotate around three axes of rotation.

An embodiment of the mechanical portion of the three-dimensional vestibular stimulation systems described herein is depicted in FIG. 2. The mechanical portion adds an additional axis of rotation around roll axis 224, in addition to pitch axis 204 and yaw axis 206.

Rotation around yaw axis 206 is mediated by yaw shaft 212. Chair 202 is rotationally supported on base 210 via yaw shaft 212. A first end 211 of yaw shaft 212 is operably linked to pitch support frame 220. Pitch support frame 220 rotationally supports roll frame 221 which rotationally supports chair 202. A second end 213 of yaw shaft 212 is rotationally associated with base 210 via gearbox 217, which contains rotational bearing system 214. Chair 202 is thus configured to rotate freely around yaw axis 206 relative to base 210.

Chair 202 is rotated around yaw axis 206 by yaw axis motor 216. Yaw axis motor 216 is operably linked to gear reducer 215, which is operably linked to gearbox 219. Gearbox 219 is operably linked to rotational shaft 212. When in operation, yaw axis motor 216 provides for rotation around yaw axis 206 in either clockwise or counter-clockwise yaw rotational directions. Further, yaw axis motor 216 can cause rotational acceleration or deceleration in either clockwise or counter-clockwise yaw directions. Rotation around yaw axis 206 can be continuous in a single rotational direction, without any limitation on the rotation characteristics or number of rotations. As discussed in more detail below, the computer system is in communication with the yaw axis motor to control acceleration, deceleration, and rotational velocity independently of the control of the other axes.

Likewise, chair 202 is operably linked to rotational base 210 via pitch shaft 218a and 218b. Pitch shafts 218a and 218b are operably associated with pitch support frame 220. Pitch shaft 218a is operably associated with 90 degree gearbox reducer 219. Support frame 220 is operably linked to base 210 through yaw shaft 212. Rotation of chair 202 around pitch axis 204 is provided by rotating the roll support frame 221 and the chair 202 together, by the pitch shaft 218a and 218b around pitch axis 204.

Pitch shaft 218a and 218b is rotated around pitch axis 204 by pitch axis motor 222. Pitch axis motor 222 is operably associated with 90 degree gearbox reducer 219, which is operably associated with pitch rotational shaft 218a. Pitch axis motor 222 can rotate chair 202 around pitch axis 204 in either clockwise or counter-clockwise pitch rotational directions. Further, pitch axis motor 222 can cause rotational acceleration or deceleration in either clockwise or counter-clockwise pitch directions. There are no intermediate hindrances to rotation of chair 202 around pitch axis 204. Rotation around pitch axis 204 thus can be continuous in a single rotational direction indefinitely, without any limitation on the rotation. The computer system is in communication with the pitch axis motor to control acceleration, deceleration, and rotational velocity independently of the control of the other axes.

Chair 202 rotates around the roll axis 224 by the roll shaft 226. Roll shaft 226 rotates by motor 230, which is operably associated with gearbox 227. Gearbox 227 is mounted in roll frame 221 and is operably associated with roll shaft 226. Roll axis motor 230 can rotate roll shaft 226 around roll axis 224 in either clockwise or counter-clockwise pitch rotational directions. Further, roll axis motor 230 can cause rotational acceleration or deceleration in either clockwise or counter-clockwise pitch directions. There are no intermediate hindrances to rotation around roll shaft 226. Rotation around roll axis 224 thus can be continuous in a single rotational direction indefinitely, without any limitation on the rotation number of rotations. The computer system is in communication with the roll axis motor to control acceleration, deceleration, and rotational velocity independently of the control of the other axes.

A subject who is treated with vestibular stimulation can be attached to chair 202 by an attachment system (not shown) during operation. Various embodiments of attachment systems can include five point harness, lap belt, head strap, ankle straps, and leg straps. Without being held to a specific embodiment, those of skill in the art will recognize that the attachment system can vary to include any attachment system known in the art provided that the spatial orientation of the subject relative to chair 202 is maintained.

In operation, rotation of chair 202 around pitch axis 204, yaw axis 206, and roll axis 224 can occur separately or simultaneously in any combination. Rotation and/or acceleration around pitch axis 204, yaw axis 206 and/or roll axis 224 produces a wider range of motion than one or two dimensional axes of rotation.

Though the embodiment of FIG. 2 depicts pitch axis 204, yaw axis 206, and roll axis 224 intersecting at a single point, those of skill in the art will recognize that in various embodiments the axes of rotation are not required to intersect. The axes can be offset relative to each other, or relative to the center of mass of the system.

Each axis of the current mechanical device can rotate freely, without mechanical impediment or positional intervention such as wiring systems. This configuration allows a dose of vestibular stimulation to be administered as a clockwise acceleration in one direction. Once a new velocity is reached, the device no longer accelerates (i.e. the acceleration is zero), and the constant velocity (with zero acceleration) can be maintained indefinitely. A angular acceleration can be produced around the same axis as the first angular acceleration by increasing the rotational velocity around the axis.

In various examples, the axes of rotation described herein are perpendicular to each other. However, those of skill in the art will recognize that the axes of rotation can be perpendicular, or offset from a perpendicular position.

Those of skill in the art will understand that in various embodiment such as those of FIGS. 1 and 2, any type of motor may be used for each of yaw axis motor, pitch axis motor, and roll axis motor, respectively. The motors can include but are not limited to servomotors, stepper motors, and electromagnetic motors. In certain embodiments, the motor can be designed to carry a load around each separate axis of rotation.

In various embodiments, the mechanical portion of various mechanical system embodiments can be operated manually, or can be operated under computer control as discussed supra.

In various embodiments of the two dimensional or three dimensional chair, pitch, yaw, and roll rotational shafts can be configured to allow power, input and output signals to be in communication with mechanical systems. For example, each shaft can be hollow and include a slip ring to allow cables, wires, and other devices to enter and leave the system. Alternatively, wireless communication devices are also employed for use of joystick controllers and other devices. An additional slip ring can be mounted in a roll rotational shaft (or any shaft to which the chair is attached) to provide power and data communications to the subject chair. Power and input and output signals can thus be controlled without limiting the range of motion of the system.

In alternate embodiments, aspects of the system can be controlled, and/or data output data can be detected, wirelessly. Motors driving various degrees of rotation can be designed to communicate with the computer system wirelessly.

C. Chair Adjustments

The chair portion of various embodiments of the systems disclosed herein can be fixed to a frame relative to each axis of rotation. The position of the chair can be fixed based on the position of the vestibular system of a particular subject. For example, the chair can be fixed to intersect pitch, yaw, and/or roll axes of rotation (depending on the degrees of rotation in the chair). Alternatively, the chair can be positioned such that the vestibular system is offset from one or more of the pitch, yaw, and roll axes of rotation.

Figure 3:
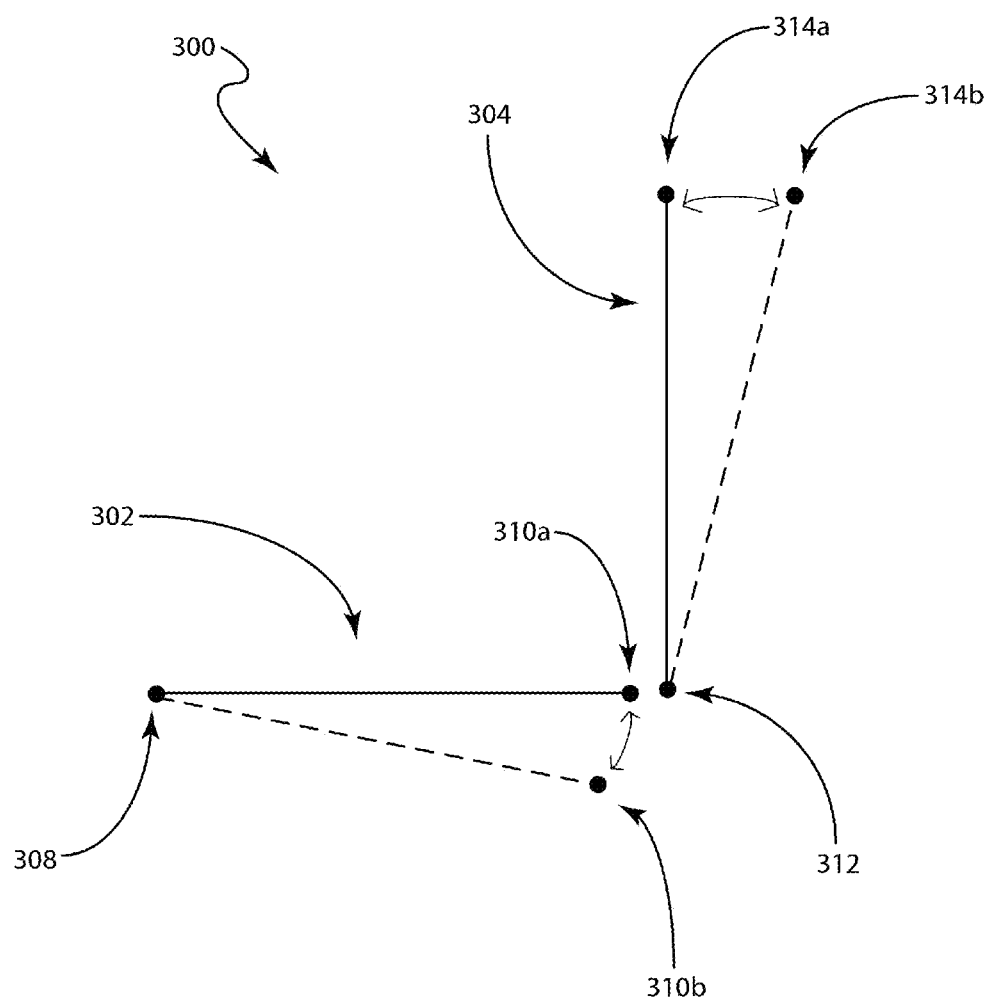
FIG. 3 depicts an adjustable chair system that can be alter the balance of the rotating device.

In alternative embodiments, the chair is an adjustable chair. FIG. 3 depicts an example of adjustable chair 300. Adjustable chair 300 includes seat portion 302 and back portion 304 both fixed to a frame. Seat portion 302 is fixed to the frame at seat pivot point 308. Seat portion 302 can rotate around seat pivot point 308 to be fixed at a point between seat lock positions 310a and 310b. Likewise, back portion 304 is fixed to the frame at back pivot point 312 to be fixed at a point between back lock positions 314a and 314b. Seat portion 302 and back portion 304 can thus adjust to alter the position of a seated subject relative to one or more axes of rotation.

The adjustable seat can be positioned to improve the balance of a seated subject relative to one or more axis of rotation. The improved balance can be adjusted to reduce the load on one or more rotational motors. By balancing the total weight of the rotating chair relative to one or more axis of rotation, the motors controlling the axis of rotation have reduced load at a given position in the rotation of the chair.

Alternatively, the position of the chair can be modified to position the vestibular system of a subject relative to one or more axes of rotation. The vestibular system is positioned in the inner ear of a subject positioned in the chair. The center of the vestibular system can thus be adjusted to intersect with, to be closer to, or to be farther from one or more axes of rotation. Alternatively, the vestibular system can be adjusted to move the vestibular system farther from the center of rotation relative to one or more axes of rotation. The position of the vestibular system relative to the axes of rotation alters the amount of rotational or linear vestibular stimulation that can be provided to a subject.

The positioning of the chair can be automated. For example, a separate motor can be operably linked to the seat back and seat bottom to adjust the chair as described in FIG. 3. In various embodiments, either a single motor or multiple motors may be used. The motors may be controlled through inputs on the chair or through the computing system either before or during stimulation.

In various embodiments, the load at various points in a rotation around one or more axes of rotation can be detected, and the seat and back portions of the chair can then be automatically adjusted by the computer to balance the load. Alternatively, the chair position can be adjusted to include another dimension of vestibular stimulation.

Those of skill in the art will understand that the variability of the chair can be adjusted using other mechanical orientations known in the art. The chair can be configured to be a single piece, with seat and back portions optionally linked.

III. Computer Architecture

In various embodiments, the multi-axis rotating device described herein can be automated using a computer system and automation software.

Figure 4:
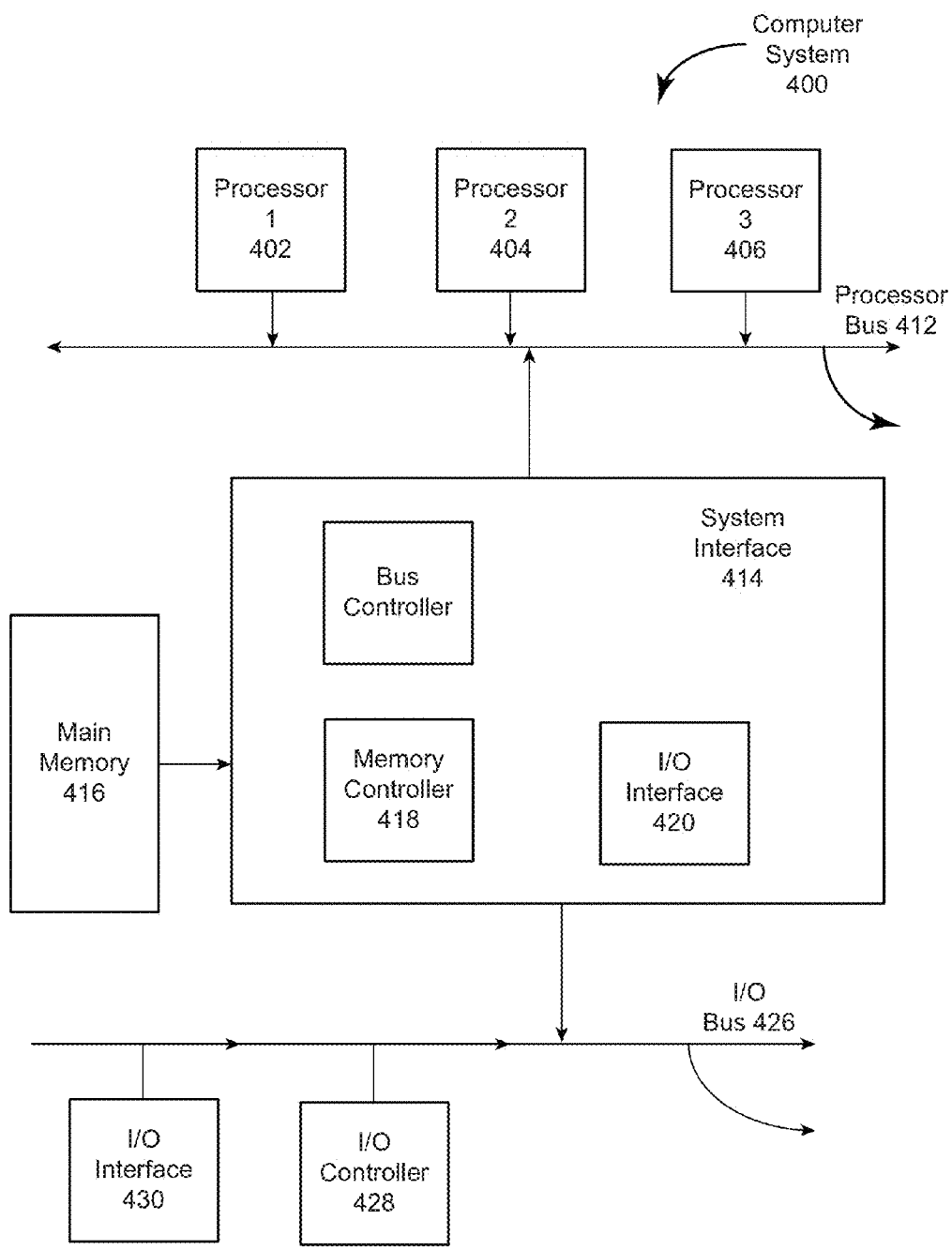
FIG. 4 depicts a block diagram illustrating an exemplary computer system designed to control a vestibular stimulation system.

FIG. 4 is a block diagram illustrating an exemplary computer system 400 which may be used in implementing control of the mechanical portion of the vestibular stimulation system. The computer system (system) includes one or more processors 402, 404 and 406. Processors 402, 404 and 406 may be responsible for processing one or more input or output signals. Processors 402, 404 and 406 may include one or more internal levels of cache (not shown) and a bus controller or bus interface unit to direct interaction with the processor bus 412. Processor bus 412, also known as the host bus or the front side bus, may be used to couple the processors 402, 404 and 406 with the system interface 414. System interface 414 may be connected to the processor bus 412 to interface other components of the system 400 with the processor bus 412. For example, system interface 414 may include a memory controller 418 for interfacing a main memory 416 with the processor bus 412. The main memory 416 typically includes one or more memory cards and a control circuit (not shown). System interface 414 may also include an input/output (I/O) interface 420 to interface one or more I/O bridges or I/O devices with the processor bus 412. One or more I/O controllers and/or I/O devices may be connected with the I/O bus 426, such as I/O controller 428 and I/O device 430, as illustrated.

I/O device 430 may include a display device (not shown), such as a cathode ray tube (CRT) or liquid crystal display (LCD), for displaying information to an end user. I/O device 430 may also include an input device (not shown), such as an alphanumeric input device, including alphanumeric and other keys for communicating information and/or command selections to the processors 402-406. Another type of user input device includes cursor control, such as a wired or wireless joystick, a mouse, a trackball, or cursor direction keys for communicating direction information and command selections to processors 402-406 and for controlling cursor movement on the display device.

System 400 may include a dynamic storage device, referred to as main memory 416, or a random access memory (RAM) or other devices coupled to the processor bus 412 for storing input or output information and instructions to be executed by processors 402-406. Main memory 416 also may be used for storing temporary variables or other intermediate information during execution of instructions by the processors 402-406. System 400 may include a read only memory (ROM) and/or other static storage device coupled to processor bus 412 for storing static information and instructions for processors 402-406.

FIG. 4 is but one possible example of a computer system that may employ or be configured in accordance with aspects of the invention. Many other possible computer systems may also employ aspects of the invention, and the invention should not be limited to this particular system.

Computer-controlled high torque drive systems can be utilized to provide rotation around any of the yaw, pitch, and/or roll axes of various embodiments with a high degree of accuracy, precision, and repeatability.

Figure 12:
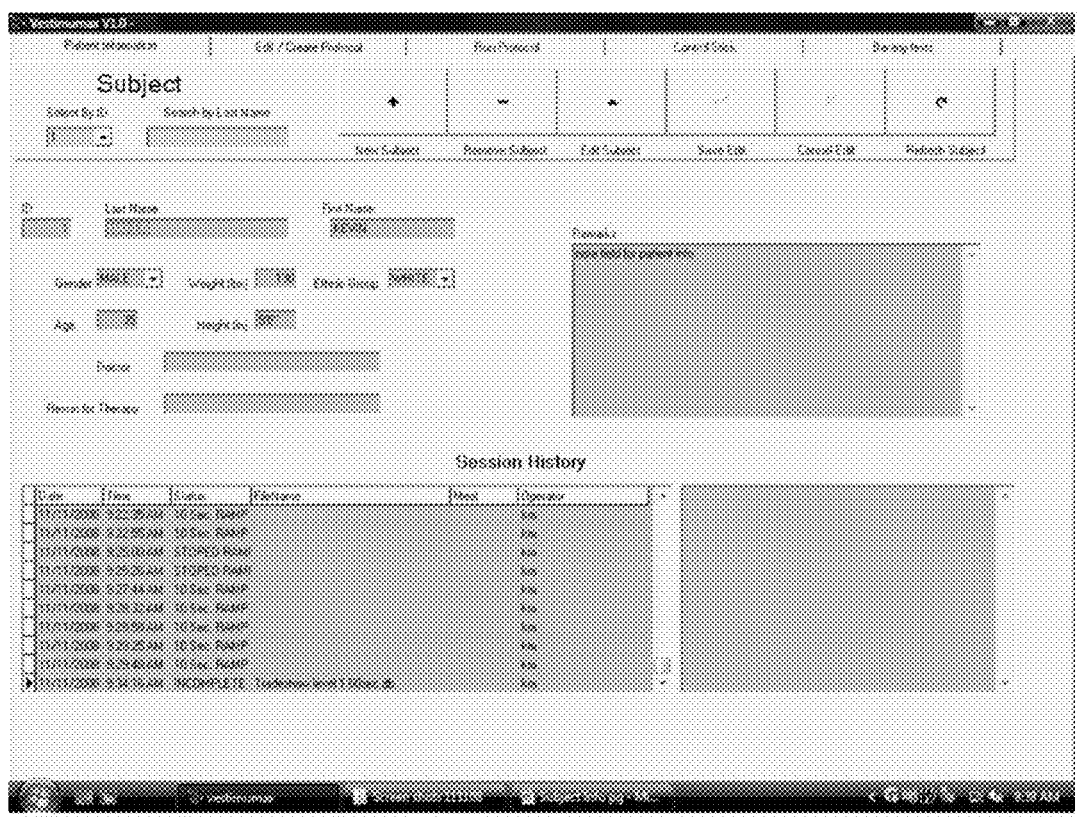
FIG. 12 depicts an embodiment of the visual layout of the input for subjects in the rotational device.

The system can also be controlled by a user display. FIG. 12 depicts an exemplary embodiment of the visual layout of the input for subjects in the rotational device. Data about the subject (or subject) can be input into the computer system.

Figure 15:
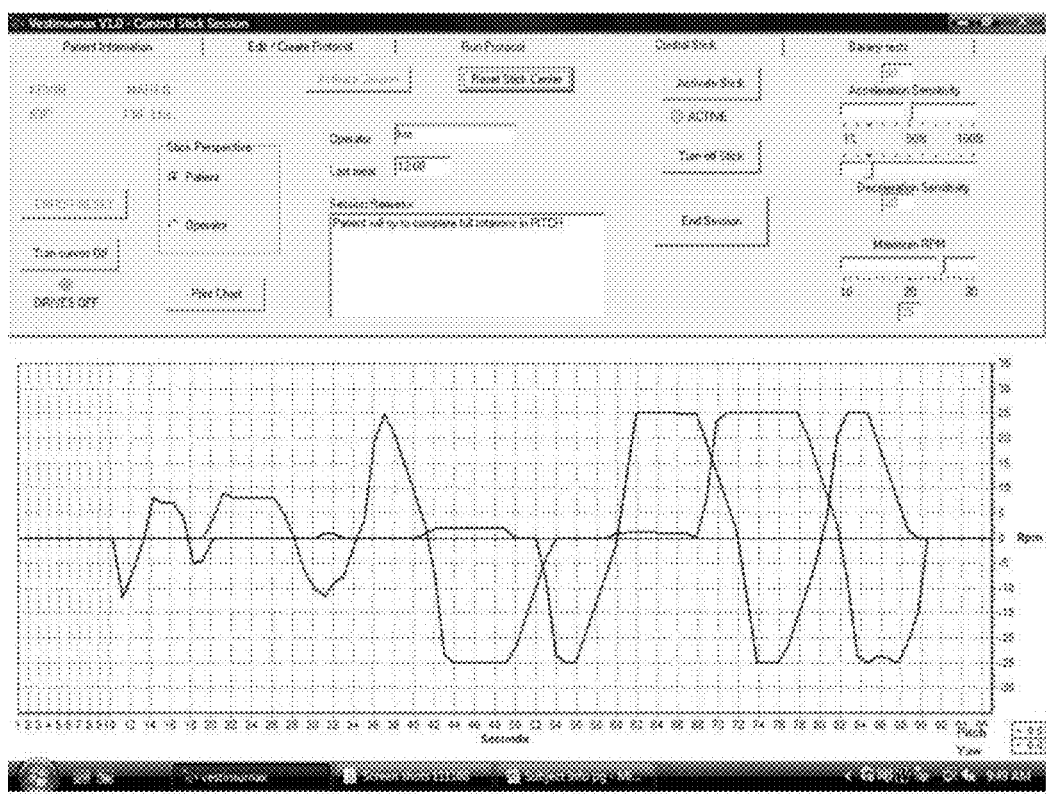
FIG. 15 depicts a movement in two dimensions by a subject under the subject's control.

In various embodiments, the acceleration, deceleration sensitivity controls are provided. FIG. 15 depicts an exemplary computer visual control of such controls. The acceleration and deceleration sensitivity controls limit the rate changes in velocity to a specific period of time. In certain applications, no limit on acceleration or deceleration control is desired, such as in certain aircraft piloting applications. In other applications, the acceleration and deceleration can be limited, such as in various video gaming embodiments in which realistic reactions to changes in acceleration or deceleration are desired, or in certain therapeutic application such as recovery from balance disorders where sudden changes in acceleration or deceleration may be detrimental.

In various embodiments, the responses to acceleration or deceleration can have a maximum rotational velocity controller. FIG. 15 depicts an example of a maximum rotational velocity controller in the form of a Maximum RPM controller. This allows for visual verification and very easy control of maximum rotation rates for the subject. Examples of uses for limiting the rotation rates include subjects having a balance disorder. Alternatively, in pilot training, subjects may wish to have a very high rotation rate for a more realistic aircraft simulation.

In various embodiments, the protocols can include an error reset controller that allows an operator to reset an error generated from the on-board motion drive controllers. An example of such a controller is also depicted in FIG. 15.

The computer controlled device allows specific protocols of vestibular stimulation to be reproduced, saved, and altered according to the needs of a specific application.

Vestibular Input Controls

Vestibular input controls can be defined externally or by the user. The controls can include the direction of rotation, acceleration, rate of velocity, time required to reach a given velocity, duration, and acceleration/deceleration sensitivity controls, as described herein.

In one embodiment, the system is controlled by a computer programmed to provide input, feedback, and motor control output signal. The computer system may be running on a conventional operating system, such as a Windows operating system. Subject medical information, including personal information about the subject can be input. Information about every therapy session a particular subject has received can thus be retained. Pre-designed parameters for operation of the vestibular stimulation system (e.g., direction of rotation, acceleration, rate of velocity, time required to reach a given velocity, and duration) can also be entered. Protocols for vestibular stimulation can be created, saved, and modified. The session can also be controlled directly from the control page. Program parameters can be compiled and plotted in graphical form to provide an illustration of the entire protocol.

Figure 5:
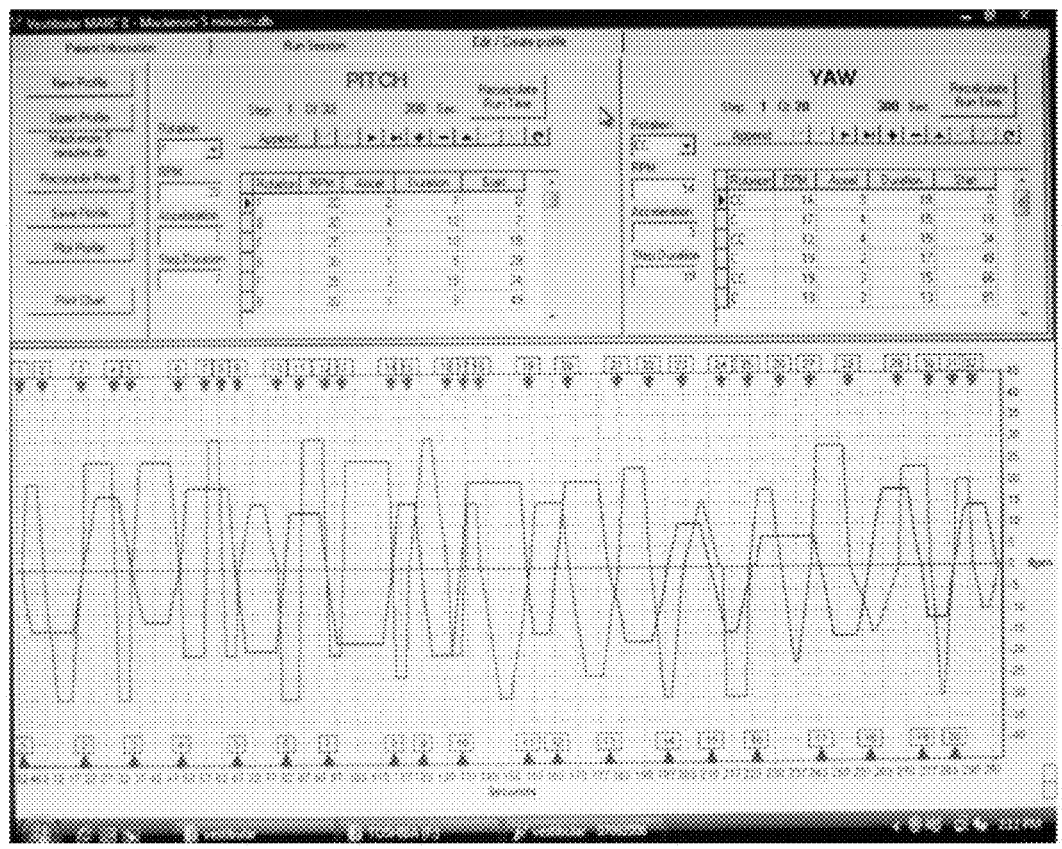
FIG. 5 depicts an exemplary vestibular stimulation dosage profile.

An exemplary vestibular stimulation dosage profile is shown in FIG. 5. The top of the screen shows the pitch tabular inputs that are either forward (F) or backward (B) directions of rotation. The user can specify the desired RPM, the acceleration up to that RPM, the duration of the spin, and the timing of the input. Similarly, the yaw inputs are categorized as clockwise (C) or counterclockwise (CC) directions of rotation, and the RPM and accelerations are specified as functions of time. The bottom of the figure shows the rotational profile in graphical form.

The software electronically captures actual rotation rates and automatically plots them real time as the therapy program is being executed. Therapy protocols are automatically dated and time stamped and saved in the subject's folder. Real time physiological data can also be captured and stored.

In various embodiments, vestibular stimulation input is controlled by the system user. For example, rotation in two or three axes of rotation is controlled via a joystick control, in which axes are controlled via x, y, and/or twist control for each of one, two or three axes of rotation.

In various embodiments, the user can input controls, for example using a conventional joystick. Pitch, roll, and/or yawl can be controlled using a controller such as a conventional joystick device. Further, the acceleration and deceleration can be controlled by the subject using the control device. Any and all parameters described herein for external controls can be accomplished using user input controls. User input controls can be used for any methods or procedures as defined herein.

Vestibular Output Controls

The computer system can store detected physiological outputs of the subject. Specifically, the computer system and software can collect human physiological and neurological streaming data from an array of sensors. For example, the heart rate, breathing pattern, skin resistivity, nystagmus, eye dilation and movement, and discomfort can all be monitored. The data can be displayed concurrently to the real time graphical representation of the applied vestibular stimuli. The physiological and neurological response applied stimuli can thus be tracked and compared in repeatable fashion to quantify subject progress over time.

IV. Doses of Vestibular Stimulation

The vestibular stimulation system provided herein can be used to administer doses of vestibular stimulation to a subject. A dose of vestibular stimulation generally refers to a defined combination of one or more variables as discussed herein, including acceleration, rate of acceleration, number of accelerations, specific duration of total accelerations, the numbers of starts and stops, and other variables discussed herein. In certain embodiments, a dose of vestibular stimulation can include the velocity of one or more of yaw, pitch and/or roll axes as appropriate for a two or three dimensional rotational system. In various embodiments, the device can be cross-coupled to include rotations around different axes. The dose of vestibular stimulation can be defined precisely and completely in terms of these variables. As used herein, "dose" and "dosage" are used interchangeably.

The vestibular stimulation system includes the ability to apply vestibular stimulation in a manner that was heretofore unachievable. Controlled rotation around one, two or three separately controlled vectors in a controlled manner using measured amounts of vestibular stimulation may be accomplished. The system can rotate through all 360 degrees in each axis in a controlled and continuous (i.e. unlimited rotations) amount.

In various embodiments, dosage of vestibular stimulation performed using the devices described herein can be defined in terms of number of variables. These variables include acceleration intensities around the pitch, roll, and yaw axes, frequency of changes of acceleration, changes of rotation direction, single axis rotation, cross-coupled multi axis rotation, rotation direction, rate of rotation, pause time, and duration of total profile. The dosage is thus a quantifiable measure of the applied stimuli. The dosage can be administered as a preprogrammed profile or profiles arising from operation by a subject (e.g. joystick operation), and by can be compared to other dosages based on the collected data of the applied stimuli. In this way, the clinician can match a dosage with the needs of the subject. Also the dosage can be used to quantify subject status and progress over time to chart the physiological capabilities of the subject.

Generally, a dose of vestibular stimulation has three parameters: intensity, frequency, and duration. In certain embodiments, vestibular stimulation from the devices disclosed herein allows the administration of doses of angular velocity, with the only change in angular acceleration incident to the velocity.

The frequency of a dose of vestibular stimulation refers to the number of changes in rotation cycles with which a subject is accelerated around a given axis or axes. A frequency of one acceleration per second refers to a single acceleration in a single direction per second of vestibular stimulation before another acceleration is applied, either in the same direction or in a different acceleration. The frequency of accelerations can be defined in terms of changes in acceleration around a single axis of rotation per period of time. Exemplary frequencies of acceleration in a dosage can be 1, 3, 5, 10, 15, 20, 25, or 30 accelerations per minute.

The intensity of a dose of vestibular stimulation relates to the acceleration, rate of acceleration, and/or maximum peak velocity or velocities around each separate axis of rotation, or the axes of rotation in combination. In various embodiments, the increase in acceleration can be represented in units of rotations per minute per second, or RPM per second. In various embodiments, the vestibular stimulation can be accelerations around one or more axes of rotation of +/−5, 10, 15, 20, 25, or 30 RPM/s. The acceleration can be represented in degrees per second squared. The dose intensity can be an additive acceleration in the same direction an axis is spinning, decelerations, or increases or decreases in velocity in one or more axes or combinations thereof.

The duration of a dose of vestibular stimulation refers to the total length of time an individual is subjected to a vestibular stimulation profile. The duration thus refers to a total number of seconds during which a given dosage profile is running.

Variables that further define a vestibular stimulation dosage includes the total changes of rotation direction of each axis of rotation, average rate of rotation, pause time before and after acceleration in one or more degrees of freedom, and the duration of total profile.

Several variables in combination can be used to define a dosage of vestibular stimulation. Because each axis of rotation in the devices described herein operate independently around a distinct axis of rotation, the intensity, frequency, and duration of angular vestibular stimulation can vary in each axis of rotation. For example, a constant and repeated dose of vestibular stimulation can be applied in a first axis of rotation, and a chaotic non-regular dose of vestibular stimulation can be applied in a second axis of rotation. Further, the dose of stimulation can be designed to affect specific semi-circular canals in the vestibular system. In embodiments of the system with two or three axes of rotation, each axis of rotation can be designed to affect individual semi-circular canals separately or simultaneously.

In various embodiments, changes in acceleration are separated by periods of constant velocity (i.e. no acceleration) in one or more axis of rotation. In some embodiments, the linear traces are shorter in duration. In other embodiments, the linear acceleration (constant velocity) traces are longer in duration.

The vestibular stimulation device can also be used to apply linear acceleration. When the center of a rotational axis of the system intersects the vestibular system of the subject, there is generally no component of linear vestibular stimulation. However, when the vestibular system is offset from any of the axes of rotation, the system creates a lever arm extending from the center of the axis of rotation to the vestibular system. The linear component of acceleration around the rotational axis is a function of the distance between the center of the axis of rotation and the vestibular system, and the acceleration around the axis. The vestibular stimulation can further be controlled linearly by altering the rotation of a subject in pitch, or alternatively independently in pitch and roll, to affect the ability of the subject to detect gravity.

Figure 7:
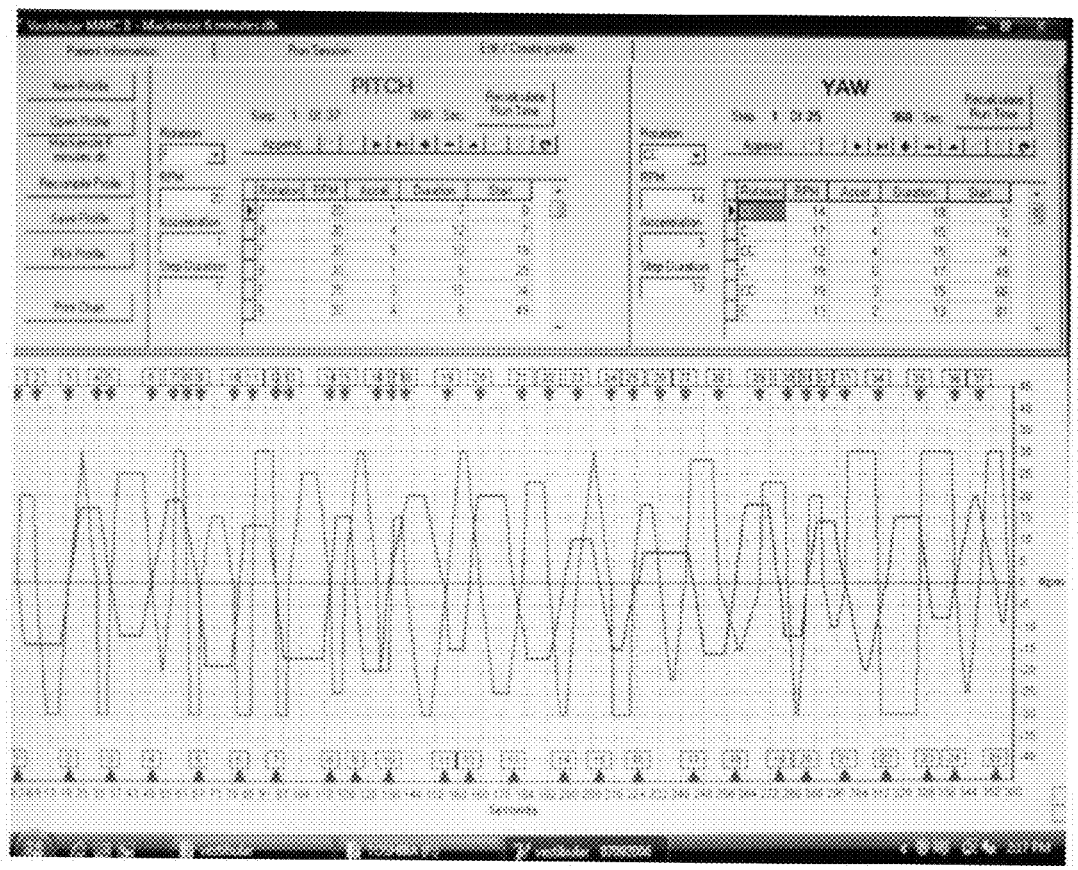
FIG. 7 depicts the time course of a chaotic high intensity dose of cross-coupled vestibular stimulation utilizing both the yaw and pitch axis of rotation.

In certain embodiments, a chaotic dose of vestibular stimulation is applied. FIG. 7 depicts an intensive chaotic dose of vestibular stimulation in a two dimensional (pitch and yaw) system. A chaotic dose refers to a series of unpredictable and arrhythmic changes in the frequency and/or intensity of the acceleration over a given duration of vestibular stimulation. The dose of FIG. 7 in pitch includes a series of rapid accelerations to 20 or 30 RPM in one second, optional equilibrations, followed by rapid decelerations (over a time course of between 1 and 5 seconds) to a constant velocity in the opposite direction.

In the chaotic dose depicted in FIG. 7, the entire dose includes 32 accelerations (positive and negative) around the pitch axis. The intensity of the doses ranges from an increase in acceleration of nearly 3 RPM/s to 30 RPM/s, and the final rotational velocity relative to the base did not exceed 30 RPM/s. The entire duration of the vestibular stimulation profile was 339 seconds. The frequency of change in acceleration varied from 1 second to 5 seconds. There was no regular repeating acceleration nor deceleration in pitch with respect to frequency, intensity, or duration.

Similarly, the chaotic dose of FIG. 7 shows numerous accelerations around the yaw axis. The yaw direction includes acceleration in both rotational directions. Rotation accelerations were slightly slower, and the final rotational velocity ranged from 5 RPM to 25 RPM. The frequency of change in acceleration varied from 1 second to 15 seconds. There was no regular repeating acceleration nor deceleration in yaw with respect to frequency, intensity, or duration.

Figure 8:
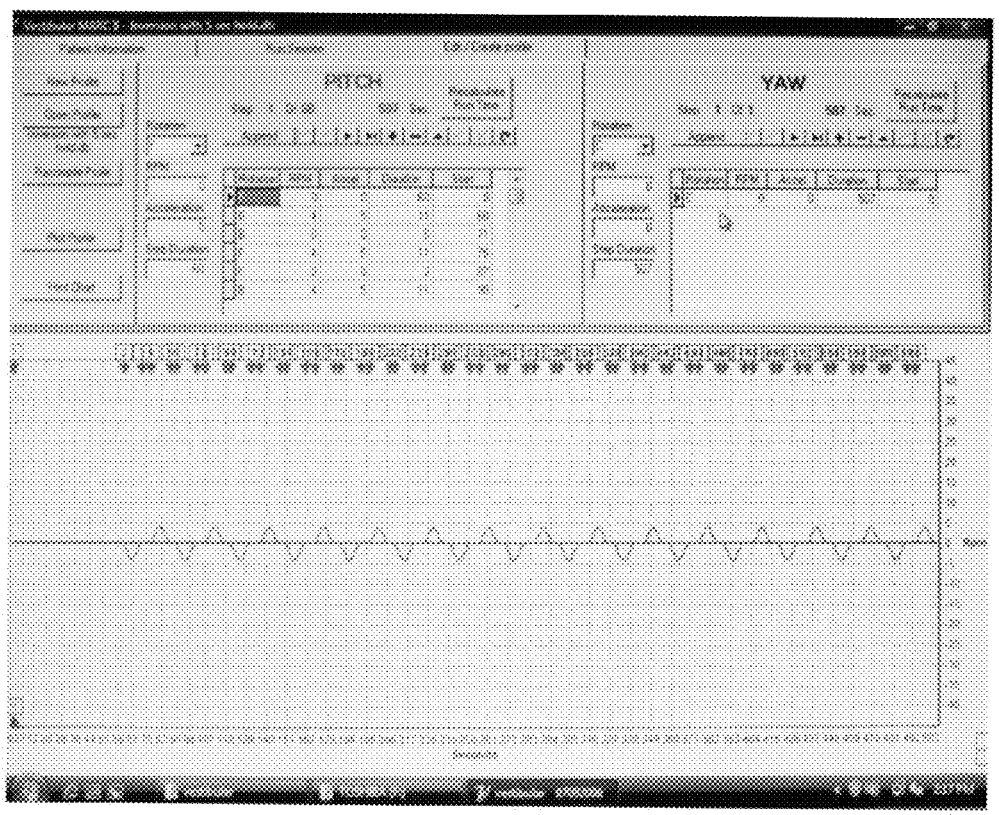
FIG. 8 depicts the time course of a regular repeating low intensity single direction dose of vestibular stimulation to provide inversion therapy.

FIG. 8 depicts a regular repeating dose of vestibular stimulation. The regular repeating dose is conducted only in the pitch axis. The pitch includes an acceleration of 0.8 RPM/s, a deceleration of 0.8 RPM/s, and a re-equilibration between acceleration and deceleration of approximately four seconds. The intensity of change of acceleration is relatively low.

Vestibular stimulation can be administered directly to a subject placed in the system described herein by an externally prepared and controlled protocol. For example, the subject has no control over the applied vestibular stimulation in the vestibular stimulation protocols of both FIGS. 7 and 8. Alternatively, a subject can control vestibular stimulation directly using a joystick controller or similar remote controller.

In computer controlled doses such as those depicted in FIGS. 7 and 8, vestibular stimulation is reproducible and recordable. The exact dose can be repeated multiple times over a period, or modified to increase or decrease one or more parameters or axis of rotation.

Doses of vestibular stimulation can be applied reproducibly using the system described herein. Though doses of vestibular stimulation can be complex in terms of the primary components (acceleration intensity, acceleration frequency, and rotation duration) and secondary components, the doses can be repeated precisely using the computer system described herein. Separate doses of vestibular stimulation can be reproduced identically. The reproducibility allows dosage protocols to be repeated precisely over a period of treatment.

When coupled with multi-axis rotation provided by the mechanical portion of the vestibular stimulation system provided herein, the increase can be synergistic due to cross-coupling effects of stimulating two or more of the semi-circular canals of the vestibular system. By continuously rotating the system in each of two or three axes, and imparting accelerations in each rotational direction, multiple canals can be targeted for variable and compounded vestibular stimulation, resulting in cross-coupled vestibular stimulation.

Vestibular stimulation can be coupled with a response test, such as a test of motor reflex control. In one embodiment, the ability of a subject to coordinate contact with a target external to the vestibular stimulation system is measured while the subject is receiving a dose of stimulation. Motor reflex control (e.g. directing a light source at an external target, using a handheld controller to control aspects of the vestibular system motion, or use a handheld controller to manipulate and external signal) can be used to measure response in a subject. Alternatively, eye or head movements can be detected to measure a response in a subject. For example, the ability to train a beam of light onto an external target can be detected, and the performance can be measured and recorded.

In various embodiments, motor responses can be compared to an independent standard for measurable outputs such as response time and/or response accuracy. In other embodiments, the response can be compared to a subject's previous standard to measure increased or decreased motor function. In other embodiments, the dose can be incrementally increased over time. If the target system and other factors remain constant, and the targeting scores increase, this would demonstrate the device has successfully improved the subject's motor reflexes. Thus, the device provides a new and quantifiable method and apparatus for motor reflex training.

Physiological responses can also be tested. These include breathing rate, skin resistivity, heart rate, eye dilation, and body temperature during a course of vestibular stimulation, as well as responses after completion of a course of vestibular stimulation. The physiological responses can be tracked and improvement can be measured, or they can be correlated to an external diagnostic.

Vestibular Stimulation Measurement

The vestibular stimulation administered to an individual can also be quantified and recorded in an index reciting various inputs. The index provides a quantifiable measure of the applied stimuli. The vestibular stimulation index can be interpreted in a matrix format, including information regarding the number of accelerations and decelerations in each direction of rotation or a combination thereof, the acceleration rates, specific duration of individual accelerations, the maximum and minimum velocities in one or more axes, any constant positions of the subject in any rotational axis, if applicable, and the total duration of vestibular stimulation.

IV. Methods of Administering Vestibular Stimulation

Vestibular stimulation can be administered to alter the response to a variety of stimuli. The response of an individual to stimuli can be used in balance training, Barany Testing, and incremental adaptation to velocity, acceleration, or any other aspect of a dose of vestibular stimulation discussed herein. In various embodiments, vestibular stimulation intensity, such as increased velocity, can be added incrementally.

Further, a number of developmental disorders can be treated using vestibular stimulation techniques. Stimulation of the vestibular apparatus in a subject's inner ear can be used to treat qualitative motor and sensory integration disorders caused by damage to the central nervous system in conditions such as, but not limited to, cerebral palsy, Down syndrome, autism, traumatic brain injury, and recovery from stroke and surgical procedures. Other conditions, such as injury recovery, can be measured.

The recovery from a disorder, neurological disorder, or injury can be tracked. Vestibular rehabilitation protocols for reduced vestibular function can be measured in terms of their adaptation, substitution, Cawthorne-Cooksey exercises and habituation.

In various embodiments, a subject can be trained to adapt to an environment over a period of time by training a subject to respond to increased levels of vestibular stimuli. For example, vestibular stimulation can be administered slowly to a subject at a low level. Vestibular stimulation intensity, as described herein, can then be increased incrementally. The dosage is controlled and, based on feedback from the subject, increased. Incremental adaptation can be used for any method of training or treatment, including therapeutic treatment, described herein.

In various embodiments, subjects can be incrementally adapted to tolerating one or more aspects of a dose and/or intensity of vestibular stimulation by provide vestibular stimulation at or below a threshold amount, or alternatively an increasing amount, in successive administrations over a period of time. The threshold can be measured, for example, by observing the subject's response to vestibular stimulation, and identifying the point at which the subject exhibits a response (whether verbal or physiological) to vestibular stimulation. Successive administrations of vestibular stimulation can be applied to allow the subject's brain to adapt to the stimuli and with successive administration of stimuli, optionally at increasing doses, to achieve increased tolerance.

The ability of a subject to adapt to an environment over a period of time can also be measured. The long-term changes in the vestibular system in response to input from head and eye movements can be measured based on conventional balance and movement tests. This approach is particularly useful for subjects with unilateral vestibular loss where the intact side of the vestibular system is trained to compensate for the loss of the contralateral labyrinth. Training is accomplished by introducing a visual error signal, and correcting that signal. Vestibular adaptation is context specific and requires training under a wide variety of movement frequencies and velocities to be successful.

In various methods, vestibular stimulation can be used for balance training. Slow exposure of vestibular stimulation can be applied to a subject. A specific pitch or yaw angle can be selected. The vestibular stimulation can be increased over a period of time. For example, the angle of pitch or frequency of pitch can be changed. The exposure of the subject to vestibular stimulation can then be increased slowly. In another method, the subject can be exposed to the same repeating motion profile many times over, thus building muscle memory for that specific maneuver.

In various methods, vestibular stimulation using the presently described systems can be used to treat motion sickness. A subject can be treated with increasing doses of vestibular stimulation that provoke motion sickness. The vestibular stimulation can be increased over a period of time to desensitize the subject to changes in motion direction. A subject's response to the vestibular stimulation can be further tested to assess and recalibrate the quantity of vestibular stimulation used to treat motion sickness in the individual.

Alternatively, vestibular stimulation using the presently described system can be used to improve spatial orientation in a subject. A subject can be treated with increasing doses of vestibular stimulation to increase the subjects ability to recognize spatial orientation. A subject's response to the vestibular stimulation can be further tested to assess and recalibrate the subject's response to spatial disorientation.

Alternatively, a dose of vestibular stimulation is applied to decrease the pathologic response. Repetitive application of vestibular stimulation (provocative stimuli) can lessen symptoms and improve function. Repetitive practice of these activities over a period of time can reduce symptoms.

Alternatively, subjects can be incrementally adapted to increasing quantities of vestibular stimulation. For example, increased increments of vestibular stimulation can be administered over a period of time. The vestibular stimulation provided to the subject allows for increasing tolerance to vestibular stimulation in the subject. This can be useful in a clinical setting, where the subject is adapting to increased quantities of vestibular stimulation, or a training setting, where the subject is adapting to increased levels of vestibular stimulation.

Vestibular stimulation can be used to administer a Barany Test. An exemplary Barany test configured for the systems and methods described herein is depicted in FIGS. 13A and 13B.

Figure 13A:
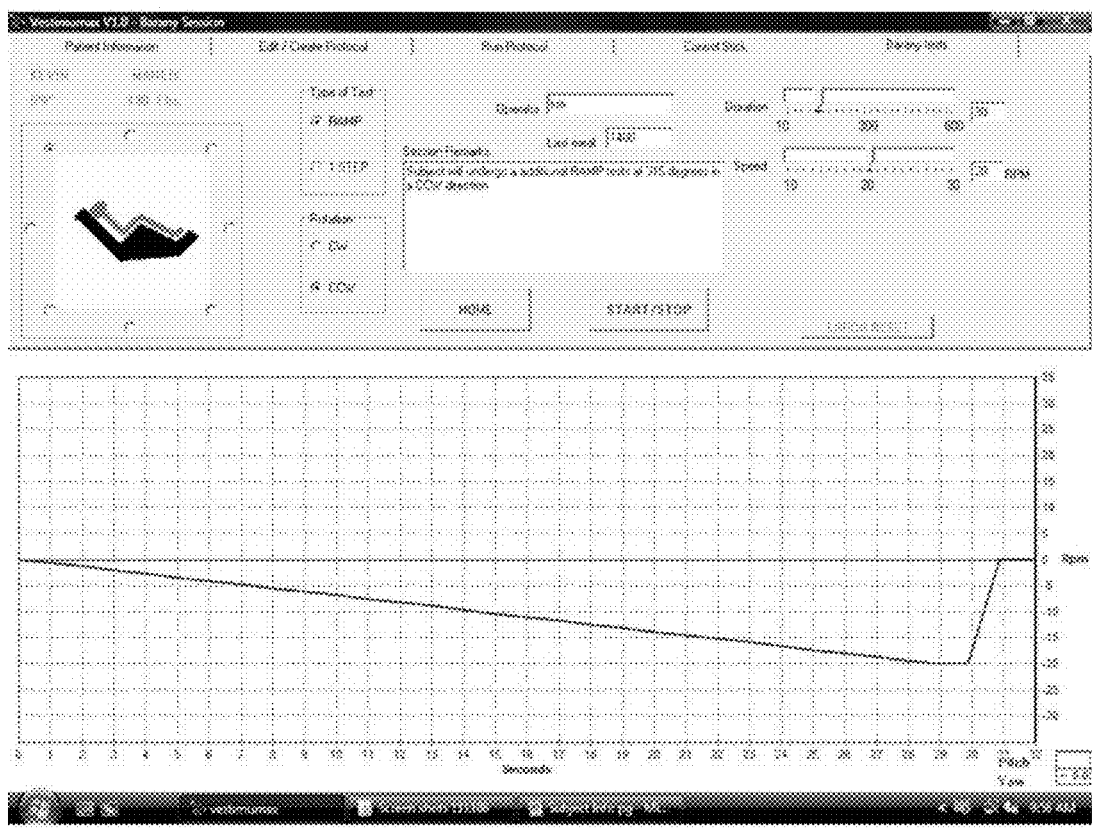
FIG. 13A depicts an exemplary Barany Test protocol using a two axis embodiment described herein.

The exemplary Barany Test includes two steps: first a slow increase in rotational velocity at constant acceleration followed by a sudden deceleration and reduction in rotational velocity, collectively depicted as (referred to as a "RAMP" step in FIG. 13A). A subject is first placed in the rotational device, and the subject's sight may or may not be limited, such as with a blindfold. In one example of the RAMP step, the subject is positioned in one of eight or more selectable positions in the pitch axis, and rotated around the yaw axis in a linearly increasing acceleration to a peak rotational velocity. The "Ramp" profile, then decelerates the subject in YAW. In certain embodiments, the sudden deceleration takes the subject to a complete stop, and automatically returns all axes to a stop position. The position in the PITCH axis, the direction of YAW rotation, the duration of YAW rotation, and the constant rotational velocity in YAW can be all automated and quantified.

In various embodiments, the acceleration around the YAW axis occurs so slowly that the subject cannot detect the velocity, direction, or speed of acceleration. The sudden deceleration results in a rush of capula in the direction of the rotational velocity. The rotation can be matched to a specific ear, and the PITCH axis can also be altered to align the subject to a specific rotation corresponding to a specific canal within the ear. The identification of a defect in the vestibular system can thus be measured.

Figure 13B:
FIG. 13B depicts a protocol of a rotational protocol.
Figure 14:
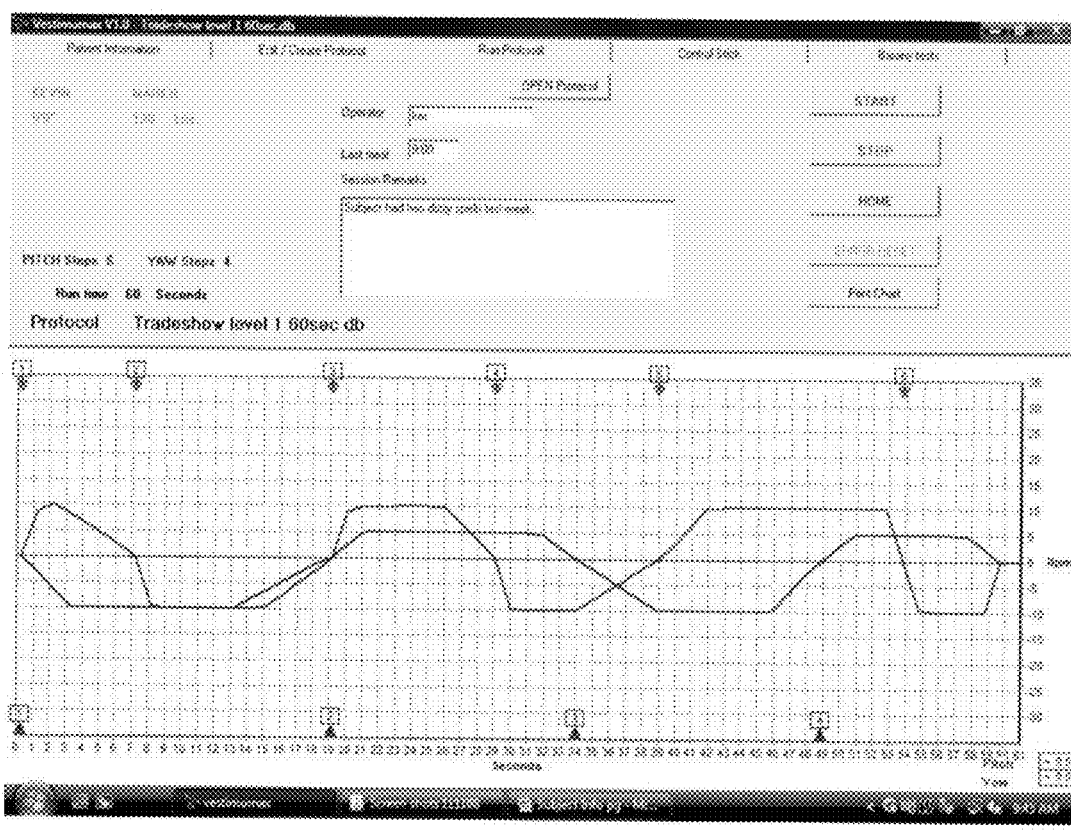
FIG. 14 depicts a layout of the computer controlled device depicted herein that includes an error reset function to allow the user to re-set errors.

A second example of a Barany Test is depicted in FIG. 13B. FIG. 13B depicts a test profile (labeled "1 STEP"), in which the subject is positioned in one of specific angle in pitch. A single step rotation profile in YAW then occurs, where the subject is rotationally accelerated around the YAW axis to a specific velocity, which is maintained for a specific period of time. The rotation around the YAW axis then decelerates, in the embodiment of FIG. 13B to a full stop. The initial angles in PITCH, the direction of YAW rotation, the acceleration rate of the YAW rotation, the speed of the YAW rotation, the duration of the steady state of the YAW rotation, and the deceleration rate of the Yaw rotation are all computer controlled, reproducible, and measurable by a computer system. The method is thus reproducible. The Barany test measurement can be made during the constant velocity by observing the results after movement of the head of the subject (by verbal feedback or physiological feedback, including but not limited to heart rate, skin resistivity, mystagmus of one or both eyes, breathing, sweating, gas, or nausea), or during the deceleration of the subject.

Cerebral Palsy

Vestibular stimulation can be applied to an individual with cerebral palsy (CP). Individuals with cerebral palsy often have dysfunctional vestibular sensory information with the brain. In many cases, individuals diagnosed with CP have dysfunctional and reduced motor control. This tends to result in sensory integration dysfunction where the vestibular system is not integrated appropriately with the brain to allow proper development of motor control, resulting in poor motor planning and output. In such cases, the subject may be restricted to a wheel chair as their only method for transportation, leaving them with no means for exercising their vestibular system. The system described herein has been designed specifically to provide vestibular stimulation treatments to subjects that are incapable of exercising their vestibular system under their own power. Subjects that had no physical way to perform vestibular exercises can be incrementally adapted to provide additional vestibular stimulation over a period of time, thus improving sensory integration and balance.

In many embodiments, CP subjects benefit from chaotic doses of vestibular stimulation having high intensity changes in acceleration in multiple directions. FIG. 7, discussed supra, depicts administration of chaotic vestibular stimulation in a two axis device. Without wishing to be limited to a particular theory or mechanism, applied vestibular stimulation provides rapid movement of the vestibular system in multiple directions. By applying sensory vestibular stimulation, CP individuals are provided with sensory input they are not otherwise able to obtain under their own power and during ordinary movements. The additional intensive vestibular stimulation provided by this device has been demonstrated to be an effective therapeutic method for subjects with CP.

Vestibular stimulation can be coupled to methods of testing and/or developing motor control in the CP subject. Various tests of motor control can be used during a dose of vestibular stimulation. Non-limiting examples of testing motor control include directing a light source (e.g. a laser pointer) at an external target, or using a handheld controller (e.g. a joystick controller) to control aspects of the vestibular system motion, or use a handheld controller to manipulate and external signal.

Improved symptoms include but are not limited to balance, head control, trunk control, speech, locomotion (reciprocal creeping), decreased rigidity, sensory integration, general attitude, and a reduction in motion sickness.

Behavioral Disorders

Many behavioral disorders manifest as a desire for vestibular stimulation. For example, behavioral disorders that manifest as hyperactive impulses, as well as "acting out" responses, can be reduced by applying active vestibular stimulation. Subjects can be incrementally adapted to vestibular stimulation as described herein.

Figure 9:
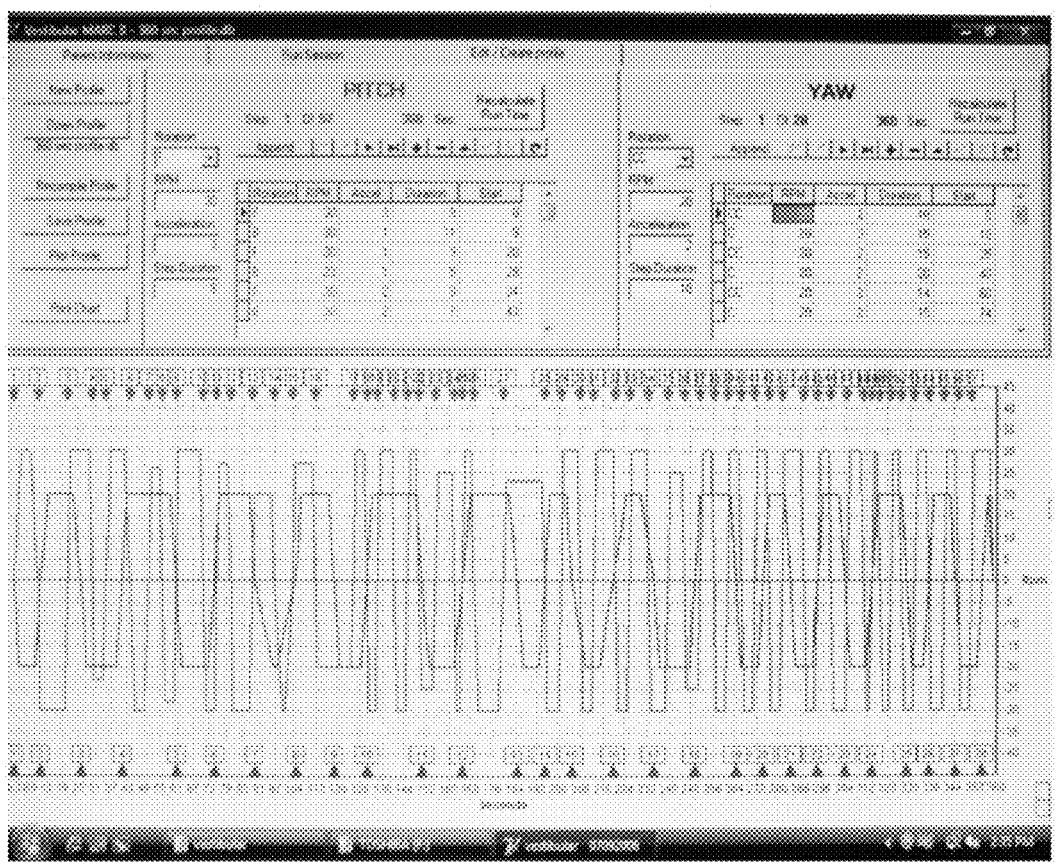
FIG. 9 depicts the time course of a chaotic high intensity dose of cross-coupled vestibular stimulation.

An exemplary dose of vestibular stimulation administered to a six year old male with behavioral disorders using a two-axis (pitch and yaw) rotating vestibular stimulation system is depicted in FIG. 9. The dose included numerous intense accelerations in different directions, ranging in magnitude of 30 RPM/s to 5 RPM/s. The frequency of change in acceleration varied from one second to five seconds. There was no regular repeating accelerations or decelerations with respect to frequency, intensity, or duration along any axis of rotation. Five weeks after the vestibular stimulation was applied, the behavioral disorders were reduced.

In other embodiments, vestibular stimulation can be tied to motor control. Various motor tests can be included. For example, spatial orientation and hand-eye coordination can be improved using a motor control and coordination test coupled to the vestibular stimulation system.

Autism

Autism is a brain development disorder that impairs social interaction and communication, and often manifests in restricted and/or repetitive behavior. Dysfunction can manifest itself in different ways. Some children may be hypersensitive to vestibular stimulation and have fearful reactions to ordinary movement activities (e.g., swings, slides, ramps, or inclines). They may also have trouble learning to climb or descend stairs or hills; and they may be apprehensive walking or crawling on uneven or unstable surfaces. As a result, they seem fearful in space. In general, these children appear clumsy. On the other extreme, the child may actively seek very intense sensory experiences such as excessive body whirling, jumping, and/or spinning. This type of child demonstrates signs of a hypo-reactive vestibular system, and are constantly trying to stimulate their vestibular systems. Different vestibular stimulation protocols can be applied to different manifestations of autism. Subjects can be incrementally adapted to vestibular stimulation as described herein.

In certain embodiments, and without being limited to any theory or mechanism, the subjects exhibiting symptoms of a hypo-reactive vestibular system move to increase the amount of vestibular stimulation. By applying an intense, high frequency, and/extended duration doses of vestibular stimulation, those individuals can improve. In certain aspects, a chaotic vestibular stimulation protocol is applied to subjects demonstrating signs of a hypo-reactive vestibular system. Exemplary chaotic vestibular doses include those depicted in FIGS. 7 and 9. For subjects who are hypersensitive to ordinary movement activity, rhythmic low dose vestibular stimulation profiles can be applied.

In other embodiments, vestibular stimulation can be tied to motor control. Various motor tests can be included. For example, spatial orientation and hand-eye coordination can be improved using a motor control and coordination test coupled to the vestibular stimulation system.

Alzheimer's Disease

Alzheimer's disease is a neurodegenerative disease most commonly manifesting in elderly people over the age of 65. Alzheimer's disease is characterized by progressive cognitive deterioration manifesting in neuropsychiatric symptoms or behavioral changes, including loss of memory, spatial disorientation and behavioral disorders.

Inversion therapy can be administered using the systems disclosed herein to control dosages of inversion therapy. The controlled dosages can be administered by altering the rate of rotation, degree of inverted position, hold time at inverted position, numbers of inversions, length of pause time at upright position between inversions, and the duration of inversion therapy session. Subjects can be incrementally adapted to tolerating one or more aspects of a dose and/or intensity of vestibular stimulation by provide vestibular stimulation at or below a threshold amount, or alternatively an increasing amount, in successive administrations over a period of time. The threshold can be measured, for example, by observing the subject's response to vestibular stimulation, and identifying the point at which the subject exhibits a response (whether verbal or physiological) to vestibular stimulation. Successive administrations of vestibular stimulation can be applied to allow the subject's brain to adapt to the stimuli and with successive administration of stimuli, optionally at increasing doses, to achieve increased tolerance.

In certain embodiments, the vestibular stimulation system is used to apply a repeated controlled inversions. An example of such inversions is depicted in FIG. 8. The dose corresponds to the number of inversions, duration of inversions, degree of inversions, and period of time a subject is held in an inverted state. Without wishing to be held to a particular mechanism or mode of action, the numerous inversions generated through the profile in FIG. 8 provide improved blood flow to the brain through repetitious expansion and contraction of the capillary blood vessels that are responsible for providing nutrients and oxygen to the brain cells.

Pilot Screening and Training

The vestibular stimulation system described herein can be used in screening and training pilots.

In one embodiment, the vestibular stimulation system described herein can be used to screen potential pilots and actual pilots for flight suitability. Subjects are exposed to a baseline profile of vestibular stimulation involving rapid changes in acceleration and disorientating rotations around multiple axes. During the accelerations and rotations, various physiological data (including, but not limited to, heart rate, breathing rate, eye dilation, salivary response, perspiration response, skin resistivity, and vestibulatory-occular reflex) are collected and analyzed. The physiological responses to such baseline tests can help indicate the subject's ability to tolerate the motion sensations of aeronautics. The response of a subject to incrementally increased amounts of vestibular stimulation can be measured over a period of time.

Figure 10:
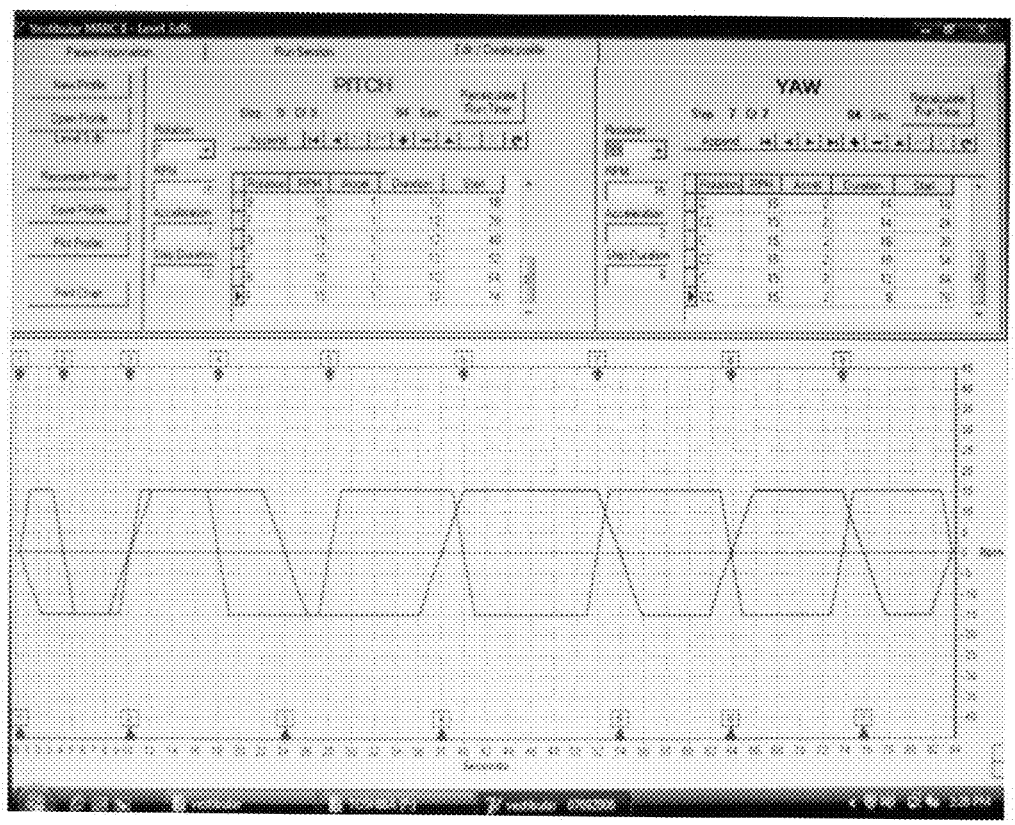
FIG. 10 depicts the time course of a regular repeating moderate intensity two axis dose of cross-coupled vestibular stimulation.

FIG. 10 depicts a dose of repeating two-dimensional vestibular stimulation. The vestibular stimulation is defined by rapid and repeated increases in acceleration around both pitch and yaw axes. Rotation about the pitch axis includes a series of accelerations at 15 RPM/s, followed by maintenance of angular velocity. A second acceleration of 15 RPM/s in the opposite direction around the pitch axis then occurs, followed by a second 10 seconds of maintaining constant velocity and zero acceleration.

Figure 11:
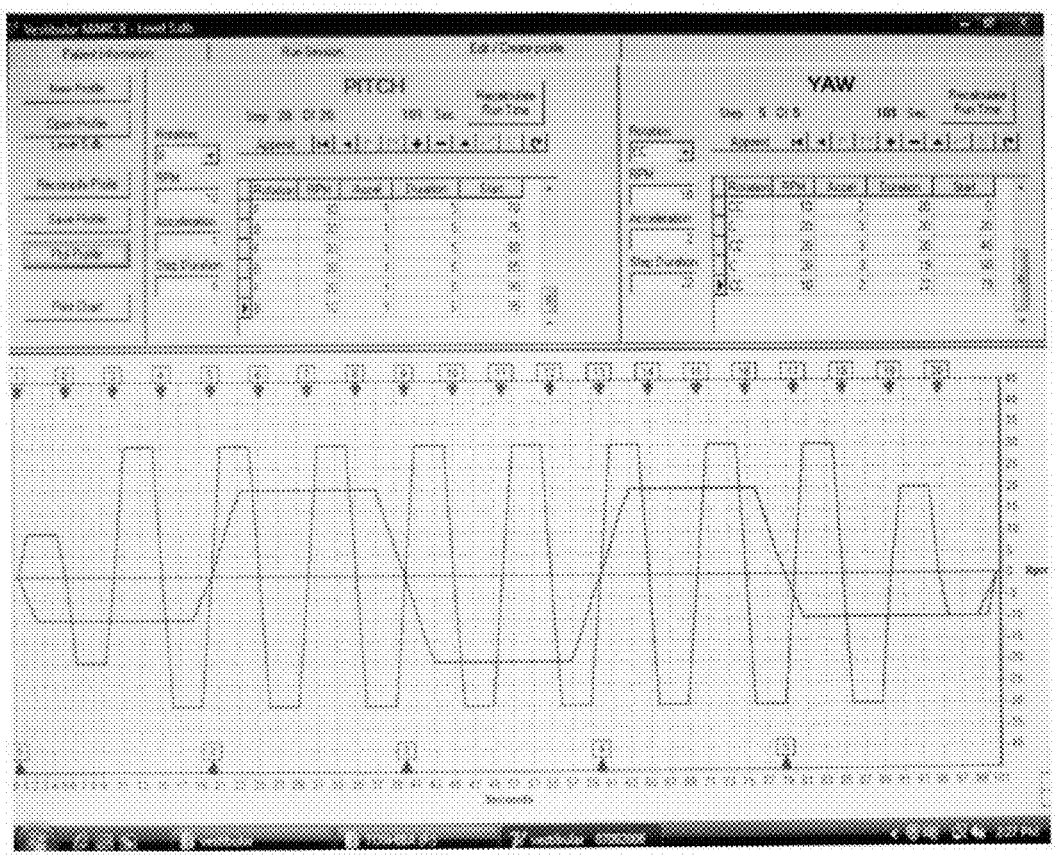
FIG. 11 depicts the time course of a regular repeating high intensity two axis dose of cross-coupled vestibular stimulation.

FIG. 11 depicts a second protocol for administering a dose of vestibular stimulation in rotations around the pitch axis and yaw axis. Like the protocol of FIG. 10, the vestibular stimulation protocol of FIG. 10 is defined by rapid and repeated increases in acceleration around both pitch and yaw axes. However, the intensity and frequency of acceleration around the pitch axis is increased over the protocol depicted in FIG. 10. Rotation about the pitch axis includes a single acceleration around the pitch axis at 30 RPM/s, followed by maintenance of rotational velocity (zero acceleration) for a period of three seconds. The subject again accelerates around the pitch axis in the opposite direction at 30 RPM/s, which is followed by a second maintenance of rotational velocity (zero acceleration). A total of 16 changes in acceleration around the pitch axis are measured. Acceleration about the yaw axis is shorter than the dose in the protocol of FIG. 10. Acceleration is at a rate of 6.6 RPM/s, followed by a constant velocity (zero acceleration) for a period of 14 seconds.

In variations that determine the suitability of new pilots, the vestibular stimulation device can be used to screen individuals suitable for pilot training. One or more physiological reactions can be measured before, during, and after administering vestibular stimulation. Thresholds for and recovery time can be determined for one or more physiological measurements. Suitability for flight training can be based on the physiological measurements.

In other variations, experienced pilots can be tested for flight suitability. One or more physiological reactions can be measured before, during, and after administering vestibular stimulation, and compared for flight suitability. The recovery time after a dose of vestibular stimulation can also be determined. The results can then be compared to previously measured responses specific to the pilot to determine suitability for flight. Incremental adaptation to vestibular stimulation over a period of time can also be accomplished.

In further variations, pilots and pilot trainees can be tested for motor control ability during vestibular stimulation. A pilot or pilot trainee can be tested for ability to maintain focus on a external to the vestibular stimulation system. Various embodiments of targeting tests include directing a light source (e.g. a laser pointer) at an external target, using a handheld controller (e.g. a joystick controller) to control aspects of the vestibular system motion, or use a handheld controller to manipulate and external signal.

The vestibular stimulation system described herein can also be used to train the vestibular system of pilots to adapt to sudden changes during flight. Different physiological measurements are detected on a pilot undergoing vestibular stimulation on the device. The physiological effects are plotted over time.

In further variations, pilots and pilot trainees can be trained to have improved motor control ability during vestibular stimulation. For example, various embodiments of targeting tests include directing a light source (e.g. a laser pointer) at an external target, using a handheld controller (e.g. a joystick controller) to control aspects of the vestibular system motion. The ability to maintain focus during vestibular stimulation is monitored and plotted.

In further variations, the physiological capabilities of pilots and pilot trainees are trained to withstand spatial disorienting flight maneuvers. For example, pilots can undergo incremental adaptation to higher levels of spatial disorienting motions in the safe and controlled environment of the systems described herein. The adaptation to higher levels of spatial disorientation train the pilot or trainee to withstand greater spatial disorienting maneuvers while in flight.

Pilots and pilot trainees can be desensitized to motion sickness by administering a training or therapeutic method called incremental adaptation. This method consists of exposing the subject to increasing amounts of the provocative stimuli so that adaptation is achieved with minimal discomfort. Incremental adaptation requires quantitative knowledge of the intensity of the applied cross-coupled stimuli and of the physiological response.

The vestibular stimulation can be adapted to specific flight occurrences that can be encountered during flight. Routine flight maneuvers, such as banking, take-off accelerations, rolls, and inversions can be modeled using embodiments of the vestibular stimulation system to model actual flight maneuvers. Non-routine flight maneuvers encountered during flight can also be modeled to determine readiness, or to train subjects to respond to the flight maneuvers. Doses of vestibular stimulation that model specific flight occurrences can then be used in conjunction with the screening or training methods described herein. Controlled acceleration or deceleration can be provided as described herein.

In various embodiments, the visual stimuli can be provided to the pilot or pilot trainee. The visual stimulation may be altered in response to computer executable instructions provided remotely by the pilot. The system can thus provide a feedback loop for pilot training.

Gaming Embodiments

The vestibular stimulation system described herein can be used in combination with visual and/or auditory stimuli, and input signals provided by the user, as part of a virtual reality simulator. Input and output signals can be transmitted to and from the subject as described herein. The subject can then respond with user input controls, including a wired or wireless joystick, a mouse, a trackball, or cursor direction keys for communicating direction information. Players can train with incrementally increasing amounts of vestibular stimulation. Controlled acceleration or deceleration can be provided as described herein. Further, subjects can be incrementally adapted to vestibular stimulation as described herein.

In various embodiments, the visual stimuli can be provided to the subject. The visual stimulation includes input signals, and are altered by the individual based on alterations in the rotation around one or more axes of rotation in an output signal. The output signal provided by the individual thus provides a feedback loop in which the subject controls a three-dimensional game.

Kits

In various embodiments, the systems described herein can be combined in a kit with instructions for their use. The kit can include any variation of the system described herein. The instructions for use can include any use described herein, including methods of use in any capacity (e.g. administering vestibular stimulation).

Variations

It should be noted that, while the embodiments described herein may be performed under the control of a programmed processor, such as processors 402-406, in alternative embodiments, the embodiments may be fully or partially implemented by any programmable or hard coded logic, such as field programmable gate arrays (FPGAs), transistor logic (TTL), or application specific integrated circuits (ASICs). Additionally, the embodiments of the present invention may be performed by any combination of programmed general purpose computer components and/or custom hardware components. Therefore, nothing disclosed herein should be construed as limiting the various embodiments of the present invention to a particular embodiment wherein the recited embodiments may be performed by a specific combination of hardware components.

While the disclosed embodiments are described in specific terms, other embodiments encompassing principles of the invention are also possible. Further, operations may be set forth in a particular order. The order, however, is but one example of the way that operations may be provided. Operations may be rearranged, modified, or eliminated in any particular implementation while still conforming to aspects of the invention. Embodiments within the scope of the present invention also include computer readable media for carrying or having computer executable instructions or data structures stored thereon. Such computer readable media may be any available media that can be accessed by a general purpose or special purpose computer (e.g. computer system 400). By way of example, and not limitation, such computer readable media can comprise RAM, ROM, PROM, EPROM, EEPROM, DVD, CD ROM or other optical disk storage, magnetic disk storage or other magnetic storage devices, or any other medium which can be used to carry or store desired program code means in the form of computer executable instructions or data structures and which can be accessed by a general purpose or special purpose computer. When information is transferred or provided over a network or another communications link or connection (either hardwired, wireless, or a combination of hardwired or wireless) to a computer, the computer properly views the connection as a computer readable medium. Thus, any such connection is properly termed a computer readable medium. Combinations of the above should also be included within the scope of computer readable media. Computer executable instructions comprise, for example, instructions and data which cause a general purpose computer, special purpose computer, or special purpose processing device to perform a certain function or group of functions.

Although various representative embodiments of this invention have been described above with a certain degree of particularity, those skilled in the art could make numerous alterations to the disclosed embodiments without departing from the spirit or scope of the inventive subject matter set forth in the specification and claims. All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. References to how components are connected (e.g., attached, coupled, connected, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected to another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A method of administering a dose of vestibular stimulation to a subject, comprising:
   administering to a subject in a two-axis rotational device a dose of vestibular stimulation,
   wherein said two-axis rotational device comprises a pitch axis of rotation directly inside a yaw axis of rotation, with the proviso that the device does not comprise a roll axis of rotation, the rotation of each said pitch and yaw axis is independent of the other axis of rotation, the rotation velocity and acceleration around each said pitch and yaw axis controlled by a computer system, and said dose comprises a measurable and repeatable pattern of acceleration intensity and frequency around said pitch axis of rotation for a first duration and said yaw axis of rotation for a second duration, said rotational device configured to allow continuous rotation through more than 360 degrees around each said axis of rotation independently and simultaneously; and
   measuring the vestibular stimulation applied to said subject by said computer system.

2. A method according to claim 1, wherein said pattern of acceleration is a chaotic pattern or regular repeating pattern around at least one of said axes of rotation.

3. A method according to claim 2, wherein the vestibular stimulation is increased by increments in successive administrations of vestibular stimulation.

4. A method of improving sensory integration in a subject, comprising administering vestibular stimulation to the subject according to claim 1, wherein the subject has a disorder or condition selected from balance disorder, cerebral palsy, Down Syndrome, autism, traumatic brain injury, and stroke.

5. A method according to claim 1, wherein the vestibular stimulation is controlled by the subject.

6. A method of claim 1, wherein the dose of vestibular stimulation comprises one or more inversions of the subject relative to the ground.

7. The method of claim 6, wherein the dose of vestibular stimulation is administered by altering one or more properties selected from the group consisting of the rate of rotation, degree of inverted position, time at said inverted position, number of inversions, length of time at non-inverted positions, and total duration of time in the rotational device.

8. The method of claim 1, wherein the mass of the subject is rotated about the center of rotation of the pitch axis of rotation and the yaw axis of rotation.

9. A system for administering vestibular stimulation to a subject comprising:
   a two-axis rotational device configured to rotate a subject around a pitch axis of rotation directly inside a yaw axis of rotation, with the proviso that the device is not configured to rotate a subject around a roll axis of rotation, each said axis operating independently and continuously from the other axis and configured to allow continuous rotation through more than 360 degrees of rotation around each said axis;
   the rotational device under the control of a computer system, the computer system including computer executable instructions to, when implemented, provide a measurable and repeatable pattern of acceleration intensity, acceleration frequency, and velocity around each said axis of rotation.

10. A system according to claim 9, wherein the computer system is further configured to provide visual stimuli to said subject.

11. A kit comprising:
    a system according to claim 9; and
    instructions for administering a dose of vestibular stimulation.

* * * * *